US006269817B1

(12) United States Patent  (10) Patent No.: US 6,269,817 B1
Nagashima et al.  (45) Date of Patent: Aug. 7, 2001

(54) BEAUTY-TREATMENT METHOD

(75) Inventors: Yoshinao Nagashima; Takahide Minami; Yukihiro Yada, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/051,489

(22) PCT Filed: Aug. 21, 1997

(86) PCT No.: PCT/JP97/02902

§ 371 Date: Sep. 21, 1998

§ 102(e) Date: Sep. 21, 1998

(87) PCT Pub. No.: WO98/07403

PCT Pub. Date: Feb. 26, 1998

(30) Foreign Application Priority Data

Aug. 21, 1996 (JP) .................................. 8-239868
Aug. 21, 1996 (JP) .................................. 8-239869
Sep. 9, 1996 (JP) .................................. 8-261346
Mar. 24, 1997 (JP) .................................. 9-070225
Mar. 24, 1997 (JP) .................................. 9-070226

(51) Int. Cl.$^7$ .............................. A61H 23/06; A61K 7/50

(52) U.S. Cl. ..................... 128/898; D24/200; 514/844

(58) Field of Search .......................... 128/898; D24/200, D24/215; 514/844, 845, 846, 847, 848

(56) References Cited

U.S. PATENT DOCUMENTS 5,266,304 * 11/1993 Baffelli et al. ................ 424/49
5,624,384 * 4/1997 Chen .

FOREIGN PATENT DOCUMENTS

WO 9916856 * 4/1999 (WO) .

OTHER PUBLICATIONS

C. Wildwood, Fragrance Journal Co., pp. 102–105, "The Aroma Therapy Massage," Oct. 1996.
Y. Imai, Reserve Co., Ltd. pp. 6–11, 16–25, 40, 50–55, 64–65, 94–95,100–101, 106–107, "New Revised Oil Massage," Oct. 1987.
Ladies Picture Report Co., Ltd., "Ladies Picture Report", pp. 230–233 and p. 235, Nov. 1994.
K. Taga, Fragrance Journal, No. 13, "Measurement of the Effects of [Esthetic Message] of Psychological and Physiological States," Mar. 1994 (with English Abstract).
Esthetic Soin, Women's Mode, Co., Published by Jyosei Mode Sha, pp. 88–89, 92–95, 98–99, "Hair Mode," Apr. 1996.
"Lee," pp. 218–221, Published by Shueisha, Dec. 1995.
T. Tanaka, et al., Published by Gakushu Kenkyu Cp/.Ltd., pp. 64–65 and pp. 158–159, "Have a Thinner Face and Thinner Arms: Face Shaping You Can Do In One Week", Jul. 1993.

* cited by examiner

Primary Examiner—David H. Willse
Assistant Examiner—Choon P. Koh
(74) Attorney, Agent, or Firm—Oblon, Spivak, McClelland, Maier & Neustadt, P.C.

(57) ABSTRACT

A cosmetic method for obtaining substantial cosmetic effects through simple massaging by ordinary people by first massaging in the direction of arterial blood flow and then in the direction of venous blood flow, or by massaging the surface of the skin with the use of a cosmetic comprising disintegrating particles while the pulse, dermal vasculature, skin temperature, or dermal blood flow is in a stimulated, dilated, elevated, or stimulated state as opposed to a resting state, and by washing the skin with a cleanser or a detergent, and then using a skincare cosmetic, wherein massaging is done using a massaging cosmetic comprising disintegrating particles before the skincare cosmetic is used after washing with a cleanser or detergent. This allows effective skincare to be achieved.

9 Claims, 14 Drawing Sheets

(FRONT)

(BACK)

(FINGER)

(FRONT)

(BACK)

(FINGER)

METHOD C

METHOD D

BEAUTY-TREATMENT METHOD

BACKGROUND OF THE INVENTION

1. Field of the Invention

The present invention relates to a beauty-treatment method in which massaging is done in the direction in which the blood flows or massaging is done while the dermal blood flow is in a stimulated state as opposed to a resting state, allowing short periods of massaging to result in considerable massaging effects and thus in pronounced cosmetic effects related to improved skin color or the like.

The present invention also relates to a cosmetic method for rapidly restoring the moisture components of skin which have been washed away when the skin is washed with a cleanser or a detergent.

2. Description of the Related Art

Beauty soaps and other detergents containing surfactants as their principal components are commonly used to wash the skin.

Detergents designed to remove soil through the action of surfactants, while effective in removing perspiration, dirt, dust and other contaminants from the skin, fail to satisfactorily remove sebum, cosmetics and other types of oily soil. In particular, contemporary foundations and other cosmetics are resistant against perspiration or water and adhere firmly to the skin, and thus cannot be adequately removed by detergents containing surfactants as their principal components. Consequently, cleansers consisting primarily of components for dissolving oily soil, such as liquid paraffin, squalane, and isopropyl myristate, are used to remove such oily soil. In such cases, the skin is washed by so-called double washing, in which oily soil is first washed away with a cleanser, and aqueous soil is then washed off with a detergent containing surfactants as its principal components.

Detergents containing both surfactants and components for dissolving oily soil have been developed recently, making it possible to remove both oily soil such as foundations and common soil such as perspiration and dust in a single washing cycle.

Washing the skin with a cleanser and a detergent, however, tends to remove the sebaceous membrane, intercellular sebum (ceramide), NMF (natural moisturizing factors), and other moisture components of the skin along with the soil.

When the sebaceous membrane is removed as a result of washing, it takes several hours to be regenerated, and no intercellular sebum or NMF is formed until the corneal layer is formed again. The skin meanwhile has lower moisture retention capacity, less defensive capacity against external stimulation, and is less soft.

After the skin has been washed with cleanser or detergents, skincare has thus been undertaken with the use of skincare cosmetics such as skin lotions, emulsions, and cremes in order to enhance the moisture retention capacity of the corneal layer of the skin, enhance dermal blood flow, promote the regeneration of the moist components of the skin, and improve skin softness.

However, despite the use of skincare cosmetics, skin tightness or luster is often lost as a result of changes in physical constitution, environment, or the like, and tightness or luster is not readily restored once it is lost.

Massaging is also sometimes attempted to address this, but massaging is known to cause wrinkling or slackness, depending on the method used. It is thus usually done by experts such as beauticians. Experts are entrusted in the direction in which massaging is done at certain massaging locations, the time needed for massaging, and the sequence of the massaging locations or the like. The massages given by experts are difficult for ordinary people to manage on their own and are hard work, which is rarely done at home.

Massages are generally done not only after the use of cleansers or detergents as described above, but also to promote blood circulation and to obtain the cosmetic effect of providing the skin with tightness or luster. Massaging is known to cause wrinkling or slackness, depending on the method used. It is thus usually done by experts such as beauticians. Experts are entrusted in the direction in which massaging is done at certain massaging locations, the time needed for massaging, and the sequence of the massaging locations or the like. The massages given by experts are difficult for ordinary people to manage on their own and are hard work, which is rarely done at home.

Because massaging promotes blood circulation and thus affords a variety of substantial beneficial effects, however, it would be desirable if ordinary people were able to manage simple massaging on their own.

A first object of the present invention is to provide a novel beauty-treatment method which resolves the aforementioned drawbacks of the prior art, which can be easily managed by ordinary people, and which affords considerable massaging effects as well as pronounced cosmetic effects.

A second object of the present invention is to achieve effective skincare by incorporating massaging that is easily managed by ordinary people in a cosmetic method comprising washing the skin and subsequent skincare.

SUMMARY OF THE INVENTION

To achieve the first of the aforementioned objects, the present invention provides a beauty-treatment method broadly divided into first and second methods.

That is, as a first beauty-treatment method, the present invention provides a beauty-treatment method comprising massaging first in the direction of arterial blood flow and then massaging in the direction of venous blood flow.

A specific embodiment of this beauty-treatment method which is proposed, particularly when the face is the massaging location, is a beauty-treatment method in which massaging is first done in such a way as to (a) describe a line from the mouth past the wings of the nose, followed by any of (b) massaging of the cheeks so as to describe a circle from the mouth, past the lower eyelids, toward the ears, (c) massaging of the forehead so as to describe an arc from between the eyebrows past the upper forehead toward either end, and (d) massaging of the lower eyelids from the inner corners of the eyes to the outer corners of the eyes; or a beauty-treatment method in which the massaging in (b), (c) and (d) is done in any sequence after the massaging in (a). Of these, a preferred beauty-treatment method for the face is a beauty-treatment method in which (a) massaging describing a line from the mouth past the wings of the nose, (b) massaging of the cheeks so as to describe a circle from the mouth, past the lower eyelids, toward the ears, and (c) massaging of the forehead so as to describe an arc from between the eyebrows past the upper forehead toward either end are done, two to three times each, in the sequence (a), (b) and (c), two to three times in succession, and (d) massaging of the lower eyelids is then done from the inner corners of the eyes to the outer corners of the eyes two to three times.

Another embodiment that is offered features the use of a cosmetic when implementing a beauty-treatment method consisting of such massaging, and in particular features the use of a cosmetic comprising disintegrating particles and, as needed, a blood circulation promoter, oil, cosmetic whitener or sebum secretion inhibitor.

As a second beauty-treatment method, the present invention provides a beauty-treatment method in which a cosmetic comprising disintegrating particles is used as a massaging cosmetic, and the massaging is done when the pulse, dermal vasculature, skin temperature, or dermal blood flow is in a stimulated, dilated, elevated, or stimulated state as opposed to a resting state.

The present invention also provides a beauty-treatment method in which a cosmetic comprising disintegrating particles is used as the massaging cosmetic, and the massaging is done during or after bathing, or during or after exercise.

Specific embodiments of the second beauty-treatment method include a beauty-treatment method in which, particularly when the face is the massaging location, massaging is first done in such a way as to (a) describe a line from the mouth past the wings of the nose, followed by any of (b) massaging of the cheeks so as to describe a circle from the mouth, past the lower eyelids, toward the ears, (c) massaging of the forehead so as to describe an arc from between the eyebrows past the upper forehead toward either end, and (d) massaging of the lower eyelids from the inner corners of the eyes to the outer corners of the eyes; or a beauty-treatment method in which the massaging in (b), (c) and (d) is done in any sequence after the massaging in (a). Of these, a preferred beauty-treatment method for the face is a beauty-treatment method in which (a) massaging so as to describe a line from the mouth past the wings of the nose, (b) massaging of the cheeks so as to describe a circle from the mouth, past the lower eyelids, toward the ears, and (c) massaging of the forehead so as to describe an arc from between the eyebrows past the upper forehead toward either end are done, two to three times each, in the sequence (a), (b) and (c), two to three times in succession, and (d) massaging of the lower eyelids is then done from the inner corners of the eyes to the outer corners of the eyes two to three times.

In the second beauty-treatment method pertaining to the present invention, a cosmetic comprising disintegrating particles is used during the massage, but a cosmetic comprising a blood circulation promoter, oil, cosmetic whitener, or sebum secretion inhibitor is also used as needed.

Also offered are methods of promoting blood circulation, improving skin color, alleviating swelling, preventing and eradicating pimples, preventing cosmetic defects, improving skin tightness, improving skin slackness, and improving make-up application by massaging with the aforementioned first and second beauty-treatment methods, as well as a massaging method for such massaging cosmetology.

To achieve the second of the aforementioned objects, the present invention provides a cosmetic method which comprises massaging with the use of a massaging cosmetic comprising disintegrating particles before a skincare cosmetic is used after the skin is washed with a detergent, in cases where the skin is washed with a detergent and a skincare cosmetic is then used.

The present invention also provides a cosmetic method which comprises massaging with the use of a massaging cosmetic comprising disintegrating particles before the skin is washed with a detergent after it is washed with a cleanser, or massaging with the use of a massaging cosmetic comprising disintegrating particles before the skincare cosmetic is used after the skin is washed with the detergent, in cases where the skin is washed with a cleanser and a detergent, in that sequence, and a skin care cosmetic is then used.

A specific method of massaging in the course of the cosmetic method pertaining to the present invention, particularly when the face is the massaging location, is a massaging method in which massaging is first done in such a way as to (a) describe a line from the mouth past the wings of the nose, followed by any of (b) massaging of the cheeks so as to describe a circle from the mouth, past the lower eyelids, toward the ears, (c) massaging of the forehead so as to describe an arc from between the eyebrows past the upper forehead toward either end, and (d) massaging of the lower eyelids from the inner corners of the eyes to the outer corners of the eyes; or a beauty-treatment method in which the massaging in (b), (c) and (d) is done in any sequence after the massaging in (a). Of these, a preferred beauty-treatment method for the face is a beauty-treatment method in which (a) massaging so as to describe a line from the mouth past the wings of the nose, (b) massaging of the cheeks so as to describe a circle from the mouth, past the lower eyelids, toward the ears, and (c) massaging of the forehead so as to describe an arc from between the eyebrows past the upper forehead toward either end are done, two to three times each, in the sequence (a), (b) and (c), two to three times in succession, and (d) massaging of the lower eyelids is then done from the inner corners of the eyes to the outer corners of the eyes two to three times.

In another embodiment of the cosmetic method pertaining to the present invention, a cosmetic comprising disintegrating particles is used during the massage, but a cosmetic comprising a blood circulation promoter, oil, cosmetic whitener, or sebum secretion inhibitor is also used as needed.

Also offered are methods of promoting blood circulation, improving skin color, alleviating swelling, preventing and eradicating pimples, preventing cosmetic defects, improving skin tightness, improving skin slackness, and improving make-up application by a cosmetic method using such massaging.

In the beauty-treatment method of the present invention for achieving the aforementioned first object, massaging is done in the direction in which the blood flows, and thus does not run counter to the direction of the muscle fibers. It therefore does not cause wrinkles or slackness, even when done by ordinary people who are not experts. The beauty-treatment method pertaining to the present invention not only features simply massaging in the direction in which the blood flows, but also features massaging first in the direction of arterial blood flow and then in the direction of venous blood flow, allowing considerable massage-based cosmetic effects to be obtained in a short period of massaging. For example, considerable massage-based cosmetic effects can be obtained by massaging about 30 seconds once a day continuously for about 3 to 6 weeks.

In the beauty-treatment method pertaining to the present invention, massaging when the pulse, dermal vasculature, skin temperature, or dermal blood flow is in a stimulated, dilated, elevated, or stimulated state as opposed to a resting state, or during or after bathing or exercise, results in greater massaging effects, and thus greater cosmetic effects, than when massaging is done in a resting state.

Implementing the beauty-treatment method pertaining to the present invention while using a cosmetic, particularly a cosmetic comprising disintegrating particles, on the skin allows even greater massaging effects to be obtained, while massages featuring the use of a cosmetic in which a blood circulation promoter, oil, cosmetic whitener, or sebum secretion inhibitor or the like has been blended as needed allow the effects of such components to be greatly enhanced. That is, when a cosmetic comprising disintegrating particles is used for massaging, the disintegrating particles gradually disintegrate during the massage, and the disintegrated particles penetrate into the scale-like protrusions and depressions of the skin surface, physically stimulating the skin depending on the particle size at that time. Here, when the cosmetic contains a blood circulation promoter, the blood circulation promoter smoothly penetrates into the skin, actively improving the peripheral circulatory system. The dermal blood flow is significantly improved by the synergistic effect of the physical and pharmacological effects of the disintegrating particles in promoting blood circulation. This prevents skin color blotching, darkness, dullness, and the like caused by poor blood circulation, and also dramatically improves skin color. These additional effects are also more evident when oils, cosmetic whiteners, or sebum secretion inhibitors are added to the cosmetic.

In the cosmetic method of the present invention for achieving the second of the aforementioned objects, meanwhile, the massaging is done before a skincare cosmetic is used after the skin is washed with a cleanser or detergent, so the skincare cosmetic is used while the blood circulation is in a significantly promoted state. This allows the skincare cosmetic to have more effective action, and can increase the moisture retention function of the corneal layer of the skin, promote better regeneration of the moist components of the skin, improve skin softness, improve tightness or slackness, and improve make-up application.

Particularly when the skin is washed with a cleanser and a detergent, in that order, and a skincare cosmetic is then used, massaging between the washing with the cleanser and washing with the detergent can provide the effect of promoting the restoration of the skin functions (such as the moisture retention function of the corneal layer, the function of regenerating the moist components of the skin, and skin softness) which are lost due to the cleanser as well as the effect of retaining the dermal function against washing with detergents. Massaging before a skincare cosmetic is used after washing with a detergent can also provide the effect of promoting restoration of skin function lost as a result of washing with a detergent.

A massaging cosmetic comprising disintegrating particles is used during the massage in the cosmetic method pertaining to the present invention, allowing greater massaging effects to be obtained in the same manner as in the massaging in the aforementioned beauty-treatment method. Massaging with the use of a cosmetic in which a blood circulation promoter, oil, cosmetic whitener, or sebum secretion inhibitor or the like has been blended as needed allows the effects of these components to be greatly enhanced.

DESCRIPTION OF THE PREFERRED EMBODIMENTS

The first and second beauty-treatment methods pertaining to the present invention as well as the cosmetic method pertaining to the present invention are described in sequence below.

In the first beauty-treatment method pertaining to the present invention, any location on the body or face may serve as the object of the massage. Whatever the location of the massage, the massaging location is basically first massaged in the direction of arterial blood flow and then in the direction of venous blood flow. In this case, the massaging location may be repeatedly massaged in the direction of arterial or venous blood flow, as long as massaging in the direction of arterial blood flow precedes massaging in the direction of venous blood flow. Alternatively, the entire massaging location may be massaged in the direction of arterial blood flow, and then any portion in the massaged location may be massaged in just the direction of venous blood flow. Again alternatively, the area may be again massaged in the direction of arterial blood flow and then massaged in the direction of venous blood flow.

Figure 1:
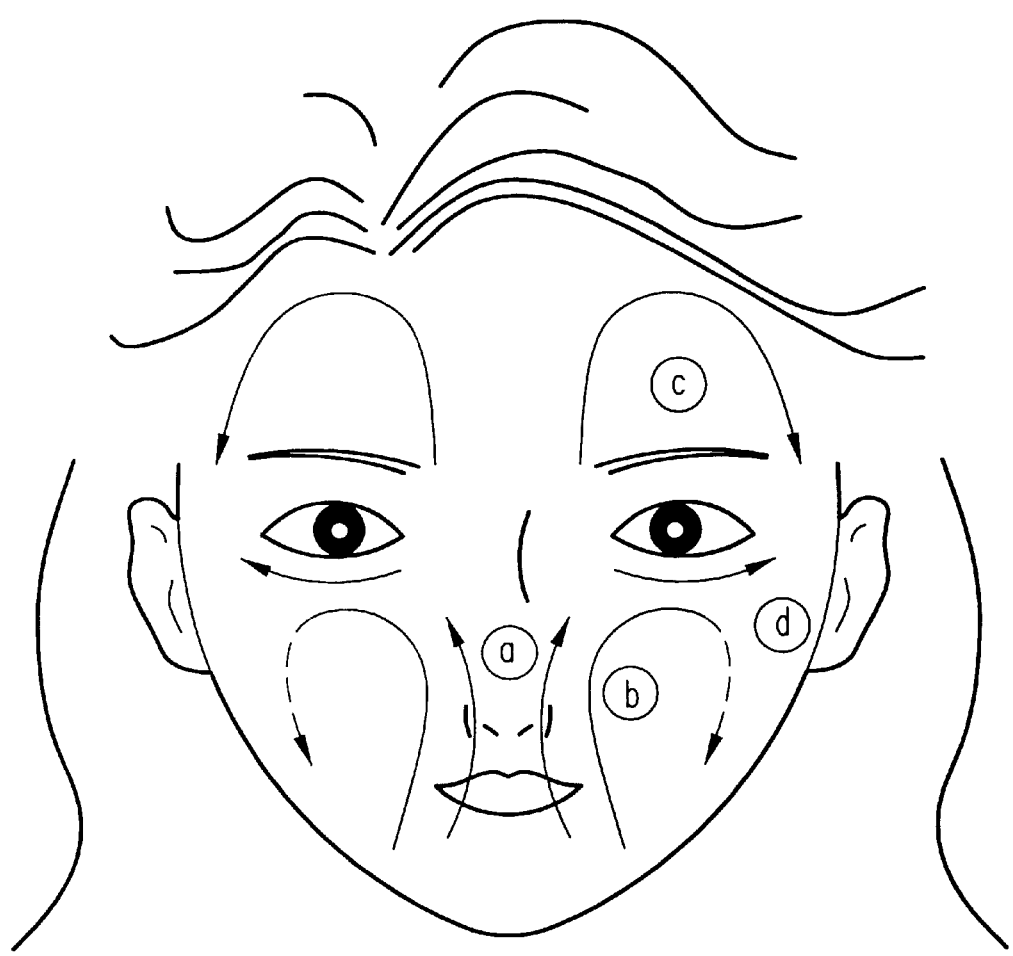
FIG. 1 is an illustration of the facial massage in the beauty-treatment method pertaining to the present invention.

For example, when the face is massaged, as shown in FIG. 1, massaging is first done (a) in the direction of facial arterial blood flow so as to describe a line from the mouth past the wings of the nose. Massaging is then done as needed in the direction of arterial blood flow where the facial arteries branch out, and then in the direction of the blood flow of the facial veins or superficial temporal veins or the veins draining therein. That is, (b) the cheeks are massaged in the direction of the blood flow of the arteria angularis and then in the direction of the blood flow of the superficial temporal veins, so as to describe a circle from the mouth past the lower eyelids toward the ears, or (c) the forehead is massaged in the direction of the blood flow of the supraorbital arteries and then in the direction of the blood flow of the superficial temporal vein, so as to describe an arc from between the eyebrows past the upper forehead toward either end, or (d) the lower eyelids are massaged in the direction of the inferior ophthalmic vein and superficial temporal veins, from the inner corners of the eyes to the outer corners of the eyes. Alternatively, the massaging in (b), (c) and (d) is done in any sequence following the massaging in (a).

As a particularly desirable method among these cosmetic massaging methods, the massaging in (a) is done two to three times, the massaging in (b) and (c) is then done, in that sequence, two to three times, and the massaging in (d) is then done two to three times. In this case, the massaging in (a) through (d) is completed in about 20 to 60 seconds.

Figure 2A:
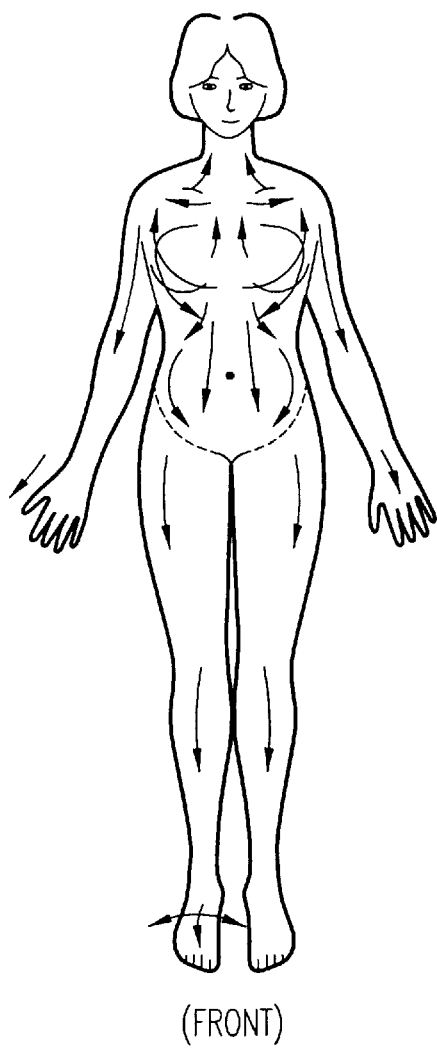
FIG. 2 is an illustration of the body massage in the beauty-treatment method pertaining to the present invention.
Figure 2B:
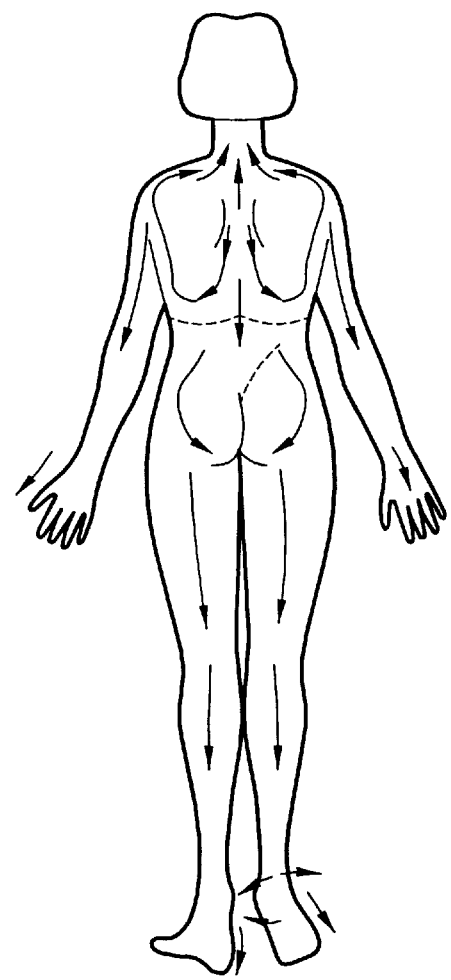
Figure 2C:
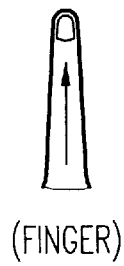
Figure 3A:
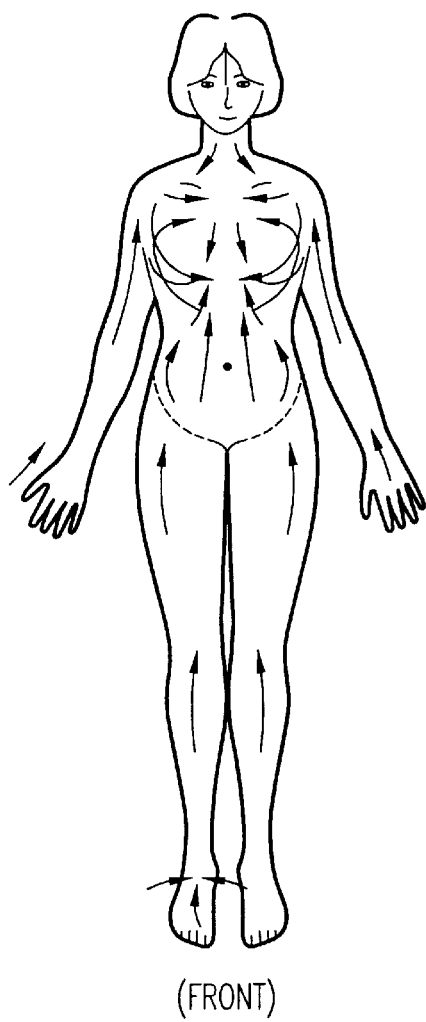
FIG. 3 is an illustration of the body massage in the beauty-treatment method pertaining to the present invention.
Figure 3B:
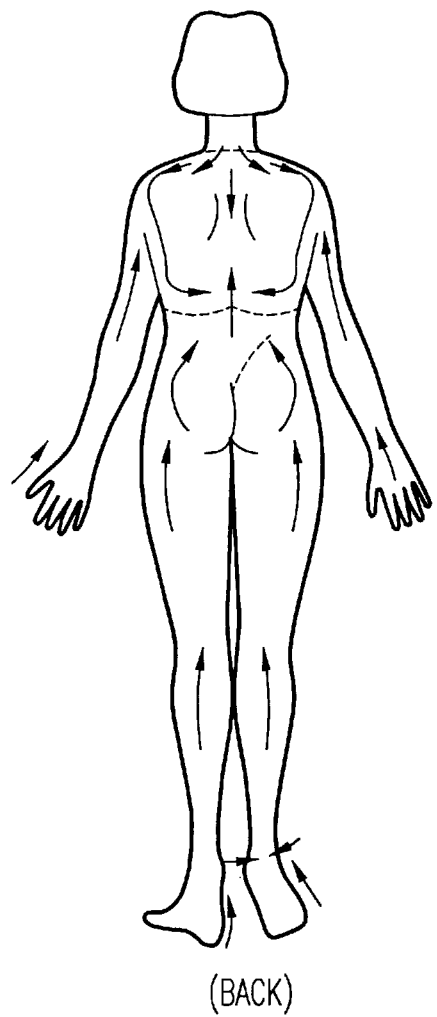
Figure 3C:
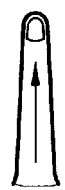

When a location other than the face, such as the body, is massaged, as shown in FIG. 2, centrifugal massaging is done from the heart along the arterial system or from the brain or spine along the nervous system, and then, as shown in FIG. 3, centripetally from the peripheral regions along the venous or lymphatic system.

In the present invention, massaging should be managed with the palms of the hands or the balls of fingers, preferably all ball of fingers, so as to slide over the skin in the massaging location.

A cosmetic is also preferably applied to the skin before the massage. Examples of cosmetics which can be used in such cases include a variety of massaging cosmetics such as massaging cremes and massaging oils, but should in particular include disintegrating particles.

Here, a variety of particles can be used as the disintegrating particles as long as they disintegrate as a result of heat, the action of water, or the friction when the cosmetic is applied to the skin. Examples include disintegrating granules obtained by the granulation of primary particles, and disintegrating microcapsules which disintegrate as a result of shear.

Examples of disintegrating granules which can be used include those consisting of water-insoluble primary particles and a binder. Here, examples of water-insoluble primary particles which can be used in the manufacture of disintegrating granules include polyethylene, polystyrene, polyester, polyvinyl chloride, polyamides, polypropylene, nylon, polyvinylidene fluoride, polyurethane, acrylic resins, polysiloxane, crystalline cellulose, starch, and organic polymer compounds of derivatives of these, or silica, alumina, talc, kaolin, titanium oxide, zinc oxide, quartz, calcium phosphate and other such inorganic powders or the like.

The primary particles may have any configuration such as spherical or amorphous configurations, but a spherical configuration is particularly preferred for the sake of safety. The average particle diameter of the primary particles is 1 to 20 $\mu$m, and preferably 3 to 15 $\mu$m. In consideration of eye safety, at least 80 wt % should be no more than 10 $\mu$m, and preferably between 4 and 10 $\mu$m.

During the manufacture of the disintegrating granules, a binder binds the aforementioned water-insoluble primary particles so as to form disintegrating granules. In this case, the bonding strength of the primary particles as a result of the binder is enough for the disintegrating granules to be readily dissolved on the skin by massaging or by friction. Specific examples of binders include fish oil, hardened castor oil, hardened rapeseed oil and other such animal and vegetable oils that are solid at ordinary temperature, ethylcellulose, acetylcellulose, nitrocellulose, hydroxymethylcellulose, hydroxyethylcellulose, hydroxypropylcellulose, polyvinyl pyrrolidone, vinyl acetate and other such organic polymer compounds.

Disintegrating granules consisting of such primary particles and binders can be formed, for example, by common methods of granulation such as fluidized bed granulation, agitated granulation, and extrusion granulation, and in particular the method (Japanese Laid-Open Patent Application 60-152407) in which the primary particles are dispersed in a water-insoluble binder, and the solvent is evaporated off, or the method (Japanese Laid-Open Patent Application 6-271417) in which a water-insoluble binder powder is mixed with primary particle granules, then granulated with a water-soluble binder, then heated to melt the water-insoluble binder powder, and cooled so as to increase the water resistance of the granules.

The particle size of the disintegrating granules thus formed is preferably 100 to 1000 $\mu$m, and even more preferably 200 to 600 $\mu$m. A particle size of less than 100 $\mu$m results in poor massaging effects, and fails to provide the pronounced effects in improving skin color or the effects in promoting blood circulation associated with the massage. A particle size of more than 1000 $\mu$m results in rough feeling and in initial stimulation too intense when rubbed into the skin.

Examples of disintegrating microcapsules which can be used include those manufactured in Japanese Laid-Open Patent Applications 59-78510, 61-282306, 1-125313 and 5-92909. Examples of capsule materials for disintegrating microcapsules include gelatin, sodium alginate, propylene alginate glycol esters, polyacrylic acid, polymethacrylic acid, methyl polyacrylate esters, ethyl polyacrylate esters, butyl polyacrylate esters, methyl polymethacrylate esters, ethyl polymethacrylate esters, butyl polymethacrylate esters, gum arabic, carboxymethylcellulose, hydroxyethylcellulose, methylcellulose, sodium polyacrylate, carboxyvinyl polymers, polyvinyl alcohols, polyacrylamides, polyvinyl pyrrolidone, ethylene polyoxide, casein, pectin, polyacrylonitrile, polyvinyl acetate, polyvinyl ether, polystyrene, agar, carrageenan, corn starch, gluten, dextrin, guar gum, locust bean gum, polyvinyl chloride, polyvinylidene chloride, polyethylene, polyethylene glycol dimethacrylate, polydivinyl benzene, polypropylene, polybutadiene and other such polymer compounds, either individually or in mixtures of two or more, or copolymers incorporating two or more monomers constituting the aforementioned polymers.

Examples of materials encapsulated in the microcapsules include the blood circulation promoters, oils, cosmetic whiteners, sebum secretion inhibitors, humectants, softeners, colorants, perfumes and solvents described below.

The particle size of the disintegrating capsules is preferably 100 to 1000 $\mu$m, and even more preferably 200 to 600 $\mu$m, in the same manner as the aforementioned disintegrating granules.

The particle size of the disintegrating particles such as disintegrating granules or disintegrating microcapsules in the present invention is the average particle diameter obtained by measurement using the light scattering method, light diffraction method, or the like.

In the first beauty-treatment method pertaining to the present invention, when massaging is done using a cosmetic containing the aforementioned disintegrating particles, the time for the massage should be the time during which the cosmetic is applied to the prescribed massaging location, the prescribed location is lightly massaged with the palms of the hands or the balls of the fingers, preferably all four fingers with the exception of the thumb, and the disintegrating particles are no longer felt. This time is usually about 20 to 60 seconds.

The cosmetic effects achieved by the first beauty-treatment method pertaining to the present invention include, specifically, effects in promoting blood circulation and various resulting effects, such as effects in improving skin color by eliminating color blotches or darkness and enhancing luster or transparency, effects in eliminating swelling, effects in preventing or reducing pimples, effects in preventing cosmetic defects, effects in improving skin tightness or slackness, and effects in improving make-up application. These effects can be even further enhanced by using cosmetics containing the aforementioned disintegrating particles during the massage. A variety of other additives can also be blended in the cosmetic containing the disintegrating particles according to the specific purpose of the massage in the present invention, including promoting blood circulation, improving skin color, reducing swelling, preventing and eradicating pimples, preventing cosmetic defects, improving skin tightness, improving skin slackness, or improving cosmetic application. The components blended in the cosmetic and the proportion in which the components are blended can be determined as desired.

For example, when attempting to obtain greater effects in improving skin color through massaging, the aforementioned disintegrating particles should be blended in an amount of 0.1 to 5 wt %, and more preferably 0.5 to 3 wt %, in the cosmetic. Less than 0.1 wt % results in poor skin color improving effects, whereas more than 5 wt % results in discomfort at the beginning of the massage.

A blood circulation promoter should be included to obtain greater skin color improving effects with the massage. Various well-known substances having an effect in promoting blood circulation can be used as the blood circulation promoter, examples of which include the vasodilator Vitamin E esters, nicotinic acid esters or orotic acid esters disclosed in Japanese Laid-Open Patent Application 62-87506, or the peripheral circulation promoter Vitamin E esters, acetic acid esters or succinic acid esters disclosed in Japanese Laid-Open Patent Application 62-195316. Nicotinic acid amides, methyl nicotinate, and the like can also be used. Examples of vegetable extracts include those disclosed as having blood circulation promoting effects in the *Fragrance Journal*, special issues No. 6 (1986) and No. 1 (1979), such as extracts of arnica, crataegus, cinchona bark, *Salvia officinalis*, *Tilia miqueliana*, *Panax ginseng*, juniper, rosemary, *Hypericum erectum*, gingko, melissa, *Ononis spinosa*, marronnier, swertia herb, garlic, camomile, thyme, field mint, nettle, cayenne, ginger, hops, common horsechestnut, lavender, carrots, mustard, cinnamon, pine, cnidium rhizome, elderberry, mountain dropwort, *Scopolia japonica*, peony, wax myrtle, Saururaceae, *nupharis rhizoma*, persimmon, marigold, corn poppy, gentian, grapes, glehnia root, orange, Chinese lemon, calamus, Japanese summer orange, witch-hazel, yellow sweetclover, common fennel, prickly mountain ash, peony root, eucalyptus, mugwort, *Isodon japanicus*, rice, *Sophora flavescens*, ginger and clove.

Of these, those that are preferred for their effects in promoting blood circulation include tocopherol nicotinate, tocopherol acetate and nicotinic acid amide, while preferred vegetable extracts include swertia herb extract, *Hypericum erectum* extract, ginkgo extract, arnica extract, witch-hazel extract, marigold extract, marronnier extract, *Isodon japanicus* extract, *Salvia officinalis* extract, glehnia root extract, rice germ oil and *Tilia miqueliana* extract, of which tocopherol nicotinate and marronnier extract are particularly desirable.

These blood circulation promoters can be used individually or in combinations of two or more, and are usually used in an amount of 0.001 to 5 wt %, and preferably 0.01 to 3 wt %, of the cosmetic.

Oils that make the skin lustrous, cosmetic whiteners that improve spots, freckles, darkness and the like associated with melanin, and sebum secretion inhibitors having effects such as the inhibition of melanin deposition in hair follicles should be simultaneously blended with the disintegrating particles, because the additional effects can be further intensified.

Here, oils that make the skin lustrous should have a refractive index of at least 1.444 or an SP value of at least 16.5 in the interests of suppressing light scattering and reflection, making the skin lustrous, and eliminating skin color blotching. Here, the SP value is a dissolution parameter calculated from the organic and inorganic properties.

Examples of oils meeting such conditions, with a refractive index of at least 1.444, include isotridecyl isononate, glycerol tri-2-ethylhexanoate, neopentyl glycol dicaprate, 1-isostearoyl-3-myristoyl glycerol, diisostearyl adipate, liquid isoparaffin, squalane, diglycerol monoisostearate, diglycerol diisostearate, diglycerol triisostearate, glyceryl tri (caprylate and caprate), isotridecyl myristate, octyldodecyl myristate, hexyldecyl myristate, octyldodecyl neodecanate, moonflower oil, jojoba oil, avocado oil, grape oil, turtle oil, mink oil, orange roughy oil and polyoxyethylene methyl polysiloxane copolymers.

Examples of oils with an SP value of at least 16.5 include isotridecyl isononate, diglycerol triisostearate, diglycerol tetraisostearate, trimethylol propane triisostearate, neopentyl glycol dioctanate, diisostearyl malate, octyldodecyl lactate, glycerol tri-2-ethylhexanoate, 1-isostearoyl-3-myristoyl glycerol, 1,3-myristoyl glycerol, and isostearyl adipate. Of these, isotridecyl isononate, neopentyl glycol dicaprate, 1-isostearoyl-3-myristoyl glycerol, glycerol tri-2-ethylhexanoate, squalane, 1,3-myristoyl glycerol, diglycerol monoisostearate, diglycerol diisostearate, diglycerol triisostearate and octyldodecyl lactate are preferred, while isotridecyl isononate, neopentyl glycol dicaprate and 1-isostearoyl-3-myristoyl glycerol are especially preferred. These oils may be used individually or in blends of two or more.

Examples of cosmetic whiteners which can be used include the common cosmetic whiteners noted in *Fragrance Journal*, special issue No. 14 (1995), such as ascorbic acid and its derivatives, hydroquinone derivatives, kojic acid and its derivatives, placenta extracts and plant extracts.

More specifically, examples of ascorbic acid and its derivatives include L-ascorbic acid phosphate ester alkali metal salts such as sodium and potassium salts of L-ascorbic acid phosphate esters; alkaline earth metal salts such as magnesium and calcium salts of L-ascorbic acid phosphate esters; trivalent metal salts such as aluminum salts of L-ascorbic acid phosphate esters; alkali metal salts of L-ascorbic acid sulfate esters such as sodium and potassium salts of L-ascorbic acid sulfate esters; alkaline earth metal salts of L-ascorbic acid sulfate esters such as magnesium and calcium salts of L-ascorbic acid sulfate esters; trivalent metal salts such as aluminum salts of L-ascorbic acid sulfate esters; L-ascorbic acid ester alkali metal salts such as sodium and potassium salts of L-ascorbic acid esters; alkaline earth metal salts such as magnesium and calcium salts of L-ascorbic acid esters; and trivalent metal salts such as aluminum salts of L-ascorbic acid esters.

Examples of hydroquinone derivatives include condensates of hydroquinone and sugars, and condensates of sugars and alkylhydroquinones obtained by the introduction of one $C_1$ to $C_4$ alkyl group to a hydroquinone.

Examples of kojic acid and its derivatives include kojic acid, kojic acid monobutyrate, kojic acid monocaprate, kojic acid monopalmitate, kojic acid monostearate, kojic acid monocinnamate, kojic acid monobenzoate and other such monoesters, and kojic acid dibutyrate, kojic acid dipalmitate, kojic acid distearate, kojic acid dioleate and other such diesters.

Examples of placenta extracts include those used as cosmetic starting materials which are generally commercially available in the form of water-soluble placenta extracts, such as those which are obtained by extracting the water-soluble components of mammalian placenta, such as that of cows, pigs, or humans, through a process such as washing, desanguination, pulverization, and lyophilization, and by then removing impurities.

Examples of plant extracts include extracts of glycyrrhiza, pueraria root, black bean, wild arum, *Tulipa eludis, Anemarrhena asphodeloides, Ophiopogon japonicus,* sansevieria, white oak, *Artemisiae capillaris flos,* camomile, artichoke, aster, rice, clove, turmeric, balsam-pear, *Dioscoreae rhizoma,* aloe, tea, strawberry saxifrage, Scutellaria root, loquat, orange peel, ginseng, althea, cinchona, comfrey, rosemary, scopolia, and gulfweed.

Of these, particularly desirable examples of cosmetic whiteners include L-ascorbic acid, arbutin, kojic acid, placenta extract, camomile extract, tea extract, pueraria root and glycyrrhiza extract. These cosmetic whiteners can be used individually or in blends of two or more.

Examples of sebum secretion inhibitors which can be used include those noted in the *Fragrance Journal* No. 10 (1994), such as anti-androgen agents, crude drug extracts, and astringents.

More specifically, examples of anti-androgen agents include oxendolone, 17-α-methyl-β-nortestosterone, chromadinone acetate, cyproterone acetate, spironolactightness, hydroxyflutamide estradiol and ethinyl estradiol.

Examples of crude drug extracts include extracts of walnut leaves, Scutellaria root, sage, hops, rosemary, *Hypericum erectum,* peppermint, camomile, *Polygonum multiflorum, Coptis japonica,* phellodendron bark, coptis rhizome, Houttuynia herb, dried orange peel, carrot, peony, Juncaceae, propolis, alisma rhizome, tannin, witch-hazel, peony, birch tree tar, royal jelly and yeast.

Examples of astringents include zinc sulfocarbolate, zinc oxide, aluminum hydroxychloride and allantoin dihydroxyaluminum.

Other examples which can be used as sebum secretion inhibitors include Vitamin B6, 13-cis-retinoic acid, Vitamin E, glycyrrhetic acid, salicylic acid, nicotinic acid, calcium pantothenate, dipotassium azelate, 10-hydroxyundecanoic acid and 12-hydroxystearic acid.

Of these, preferred examples of sebum secretion inhibitors include estradiol, zinc sulfocarbolate, zinc oxide, royal jelly, 10-hydroxyundecanoic acid and 12-hydroxystearic acid. These sebum secretion inhibitors can be used individually or in blends of two or more.

Examples of cosmetics used for massaging in the beauty-treatment method of the present invention include, in addition to the aforementioned components, various components used in common ointments, detergents, massaging agents, and the like, such as humectants, softeners, surfactants, corneal layer protectants, thickeners, preservatives, pH regulators, perfumes, antioxidants, dyes, active pharmacological components and solvents.

Examples of humectants include ethylene glycol, diethylene glycol, triethylene glycol and other polyethylene glycols, propylene glycol, dipropylene glycol, and other propylene glycols, 1,3-butylene glycol, 1,4-butylene glycol and other butylene glycols, glycerol, diglycerol, and other polyglycerols, sorbitol, mannitol, xylitol, maltitol and other such sugar alcohols, glycerol ethylene oxide (hereinafter abbreviated as EO) and propylene oxide (hereinafter abbreviated as PO) adducts, sugar alcohol EO and PO adducts, adducts of EO or PO and monosaccharides such as galactose and fructose, adducts of EO or PO and polysaccharides such as maltose and lactose, sodium pyrrolidonecarboxylate, and polyoxyethylene methyl glycoside (EO addition mols=10, 20, or the like).

Examples of softeners include α-hydroxyisobutyric acid, α-hydroxyisocaproic acid, α-hydroxy-n-caproic acid, α-hydroxyisocaprylic acid, α-hydroxy-n-caprylic acid, α-hydroxy-n-capric acid, lactic acid, α-hydroxystearic acid, citric acid, glycolic acid and other such α-hydroxy acids, lysine, arginine, histidine, ornithine, canavanine and other basic amino acids, ε-aminocaproic acid, urea, 2-hydroxyguanidine, 2-(2-hydroxyethoxy)ethylguanidine and other such amines, as well as the peptides noted in Japanese Laid-Open Patent Applications 62-99315 and 2-178207, and the trimethyl glycerol noted in Japanese Laid-Open Patent Application 6-293625.

Examples of surfactants include polyoxyethylene (hereinafter abbreviated as POE), hardened castor oil, POE alkyl ethers, POE branched alkyl ethers, POE fatty acid esters, POE glycerol fatty acid esters, POE sorbitan fatty acid esters, POE sorbitol fatty acid esters, POE hardened castor oil alkyl sulfate esters, POE alkyl sulfate esters, polyglycerol fatty acid esters, alkylphosphate esters, POE alkylphosphate esters, aliphatic alkali metal salts, sorbitan fatty acid esters, glycerol fatty acid esters, alkyl polyglycosides, polyethylene glycol fatty acid esters, α-monoisostearyl glycerol ethers, stearoyl sodium methyltaurate, POE lauryl ether sodium phosphate, and ether-modified silicone.

Examples of corneal layer protectants include hyaluronic acid, chondroitin sulfate and other such mucopolysaccharides, gelatin, collagen and other such proteins, and the acidic hetero polysaccharides noted in Japanese Laid-Open Patent Application 64-10997.

Examples of thickeners include carrageenan, dextrin, methylcellulose, ethylcellulose, hydroxyethylcellulose, hydroxypropylcellulose, polyvinyl alcohol, polyacrylic acid, sodium polyacrylate, methacrylic acid, carboxyvinyl polymer, xanthan gum, carboxymethyl chitin, chitosan, cationized cellulose and other such polymer compounds, magnesium aluminum silicate, bentonite and other such inorganic compounds.

When a cosmetic is used for massaging in the first beauty-treatment method pertaining to the present invention, cosmetics consisting of the aforementioned components may be in either liquid or solid form, but are preferably used as liquids in containers from which they are discharged in constant amounts. This allows suitable constant amounts to be discharged by a simple operation during the massage. Here, a liquid state includes any of cremes, pastes, gels, O/W emulsions and W/O emulsions. Here, the diameter of narrowest conduit of the container used to discharge constant amounts of the cosmetic must be greater than the particle diameter of the disintegrating particles contained in the liquid cosmetic, in order to prevent the container from closing up and poor discharging of cosmetic. The type of such a container for discharging constant amounts is not particularly limited, and examples include pump containers and metering containers.

Of these, pump containers have a pump chamber consisting of a cylinder and piston, where the vertical operation of the piston discharges a constant amount of the determined cosmetic depending on the volume of the pump chamber. There are various types of pump containers, which can be widely used in the present invention.

In the second beauty-treatment method pertaining to the present invention, massaging is done when the pulse, dermal vasculature, skin temperature, or dermal blood flow is in a stimulated, dilated, elevated, or stimulated state as opposed to a resting state in order to enhance the cosmetic effects obtained by the massage. Because of individual variation in the resting pulse, dermal vasculature, skin temperature, and dermal blood flow state, in the present invention a pulse in a stimulated state as opposed to a resting state is determined on the basis of the resting state of the individual receiving the massage. The pulse is usually 60 to 100 beats/min in a resting state, the skin temperature is 33 to 35° C., and the dermal blood flow is 30 to 150 mL/min/100 g, so a level beyond these levels is considered a stimulated state in the present invention. The ratio between the vascular thickness and inside diameter are reduced when the vessels dilate, so a dilated dermal vascular state can be determined on the basis of the value for the "vascular thickness"/"vascular inside diameter." In the capillaries, for example, a value of vascular thickness/vascular inside diameter$\leq 1/5$ can usually be defined as a stimulated state.

In the second beauty-treatment method pertaining to the present invention, massaging is done when at leastightness of the pulse, dermal vasculature, skin temperature, or dermal blood flow is in a stimulated state as opposed to a resting state. The pulse or the like is in a stimulated state during or after bathing or exercising in terms of actual activity. The present invention thus includes massaging during or after bathing or exercising.

In the second beauty-treatment method pertaining to the present invention, the object of massaging is any location on the body and face, just as in the first beauty-treatment method pertaining to the present invention. Although the direction of the massage, the number of times the massaging is done, the sequence of the massaging locations, and the like are not particularly limited, all locations are preferably massaged in accordance with the aforementioned massaging method in the first beauty-treatment method of the present invention.

In the second beauty-treatment method pertaining to the present invention, various massaging cosmetics such as massaging cremes and massaging oils can be used on the skin in advance during the massage, although cosmetics including disintegrating particles are used in particular. Here, the aforementioned disintegrating particles or cosmetics containing disintegrating particles can be used, allowing the aforementioned massaging effects to be obtained.

In the second beauty-treatment method pertaining to the present invention, when massaging is done using a cosmetic containing the aforementioned disintegrating particles, the time for the massage should be the time during which the cosmetic is applied to the prescribed massaging location, the prescribed location is lightly massaged with the palms of the hands or the balls of the fingers, preferably all four balls of the fingers with the exception of the thumb, and the disintegrating particles are no longer felt, in the same manner as in the first beauty-treatment method of the present invention. This time is usually about 20 to 60 seconds.

The cosmetic effects achieved by the second beauty-treatment method pertaining to the present invention include, specifically, effects in promoting blood circulation and various resulting effects, such as effects in improving skin color by eliminating color blotches or darkness and enhancing luster or transparency, effects in eliminating swelling, effects in preventing or reducing pimples, effects in preventing cosmetic defects, effects in improving skin tightness or slackness, and effects in improving make-up application. A variety of additives can also be blended in the cosmetic used in the massage according to the specific purpose of the massage in the present invention, including promoting blood circulation, improving skin color, reducing swelling, preventing and eradicating pimples, preventing cosmetic defects, improving skin tightness, improving skin slackness, or improving cosmetic application. The components blended in the cosmetic and the proportion in which the components are blended can be determined as desired, preferably in accordance with the aforementioned first beauty-treatment method.

In the second beauty-treatment method pertaining to the present invention, the cosmetics that are used may be in either liquid or solid form, but are preferably used as liquids in containers from which they are discharged in constant amounts, just as in the first beauty-treatment method.

When the skin is washed with a detergent and a skincare cosmetic is then used in the cosmetic method pertaining to the present invention, massaging is done with the use of a massaging cosmetic comprising disintegrating particles before the skincare cosmetic is used after the skin is washed with a detergent. When the skin is washed with a cleanser and a detergent, in that sequence, and a skincare cosmetic is then used, massaging is done with the use of a massaging cosmetic comprising disintegrating particles before the skin is washed with a detergent after it is washed with a cleanser, or massaging is done with the use of a massaging cosmetic comprising disintegrating particles before the skincare cosmetic is used after the skin is washed with the detergent.

Here, examples of cleansers used to wash the skin include various conventional types which wash off the oily soil of foundations and the like, such as emulsions, skin lotions, oils, or gels which contain a primary component such as liquid paraffin, squalane, Vaseline, beeswax, cetanol, stearic acid, cetyl alcohol, propylene glycol or glycerol.

Examples of detergents include various conventional types used to clean away sebum, perspiration and dirt. Examples include weakly alkaline cosmetic soaps consisting primarily of fatty acid alkali salts, as well as weakly alkaline tightnessutral cleansing foams, body shampoos and hand soaps consisting primarily of surfactants such as monoalkyl phosphates, sodium acylglutamates, fatty acid alkylol amides and amine oxides.

Examples of skincare cosmetics used after the skin has been washed include conventionally used skincare cosmetics such as skin lotions, emulsion and cremes. Because the absorption of moisturizing components is promoted when the skin is softened, the use of a skin lotion followed by the use of an emulsion or creme is particularly preferred.

Examples of skin lotions that can be used here include moisturizing skin lotions, astringent skin lotions and softener skin lotions. Examples of emulsions which can be used include emollient lotions, nourishing lotions, moisture lotions and milky lotions. Examples of cremes which can be used include emollient cremes, nourishing cremes, base cremes, cold cremes and moisture cremes.

In the cosmetic method pertaining to the present invention, massaging is done before the use of the skincare cosmetic after the skin has been washed with a cleanser or detergent. Such a cosmetic method can be applied to any location on the body and face. Accordingly, any location on the body and face may serve as an object of massaging done in the course of the cosmetic method pertaining to the present invention.

Although the direction of the massage, the number of times the massaging is done, the sequence of the massaging locations, and the like are not particularly limited in the massaging method, all locations are preferably massaged in accordance with the aforementioned massaging method in the first beauty-treatment method of the present invention.

A cosmetic containing disintegrating particles is used as a massaging cosmetic during the massage in the cosmetic method pertaining to the present invention. Here, the aforementioned disintegrating particles or cosmetics containing disintegrating particles noted in the first beauty-treatment method of the present invention can be used, allowing the aforementioned massaging effects to be obtained, just as in the second beauty-treatment method of the present invention.

In the cosmetic method pertaining to the present invention, when massaging is done using a cosmetic containing the aforementioned disintegrating particles, the time for the massage should be the time during which the cosmetic is applied to the prescribed massaging location, the prescribed location is lightly massaged with the palms of the hands or the balls of the fingers, preferably all four balls of the fingers with the exception of the thumb, and the disintegrating particles are no longer felt, in the same manner as in the first and second beauty-treatment methods of the present invention. This time is usually about 20 to 60 seconds.

In the beauty-treatment method of the present invention, massaging with the use of the aforementioned massaging cosmetics, or the use of a skincare cosmetic following such massaging, can increase the moisture retention function of the corneal layer, and can promote blood circulation and thus rapidly restore moist components of the skin, as well as various other effects associated with the effects in promoting blood circulation, such as effects in improving skin tightness or slackness, effects in improving cosmetic application, effects in preventing cosmetic defects, effects in improving skin color by eliminating color blotches or darkness and enhancing luster or transparency, effects in eliminating swelling, and effects in preventing or reducing pimples. These effects can be even further enhanced by blending various additives in the massaging cosmetic containing the disintegrating particles as needed. The components blended in the massaging cosmetic and the proportion in which the components are blended can be determined as desired, but are preferably managed in the same manner as in the aforementioned first beauty-treatment method.

The configuration of the massaging cosmetics that are used in the cosmetic method of the present invention may be the same as in the aforementioned first and second beauty-treatment methods, and they are preferably used as liquids in containers from which they are discharged in constant amounts.

TEST EXAMPLES

The present invention is described in greater detail below with reference to test examples.

Test Example 1

Twenty normal females in their forties were divided into two groups, cosmetics having the composition in Table 1 were used as the massaging cosmetic, and methods A (Test Example 1-1) and B (Test Example 1-2) were completed once in 30 seconds, once a day for six weeks in the bathroom in the following manner for each group. The dermal blood flow, darkness index, and tightness index were compared in the following manner before and six weeks after massaging was begun with these methods. The results are given in FIGS. 4 through 6.

TABLE 1

| Massaging cosmetic | (wt %) |
|---|---|
| purified water | 89.9 |
| disintegrating granules (*1) | 1.0 |
| blood circulation promoter: nicotinic acid-d1-α-tocopherol | 1.0 |
| polyoxyethylene hardened castor oil | 1.0 |
| carboxyvinyl polymer | 0.5 |
| 3% water-soluble collagen liquid | 1.0 |
| glycerol | 5.0 |
| L-arginine | 0.5 |
| methyl p-hydroxybenzoate | 0.1 |

(*1) Prepared in accordance with the method noted in Japanese Laid-Open Patent Application 6-271414 using disintegrating granules: 91 wt % polyethylene powder as primary particles (mean particle diameter: 5 μm), 3 wt % hardened rapeseed oil as the binder, and 6 wt % hydroxypropylcellulose.

Method A (Test Example 1-1)

(A-1) Approximately 2 mL cosmetic was placed in the palm of the hand and applied over the entire face.

(A-2) All four fingers of both hands (index finger through pinky) were used to massage two to three times so as to describe a line from the mouth past the wings of the nose (see direction (a) in FIG. 1).

(A-3) Massaging was done two to three times so as to describe a circle from the center of the cheeks to the outside (see direction (b) in FIG. 1).

(A-4) Massaging was done two to three times so as to describe an arc from the center of the forehead to the outside (see direction (c) in FIG. 1).

(A-5) (A-2) through (A-4) were repeated three times.

(A-6) The area under the eyes was massaged toward the outside three times so as to describe a gradual arc (see direction (d) in FIG. 1).

(A-7) Washed with lukewarm water.

Method B (Test Example 1-2)

(B-1) Approximately 2 mL cosmetic was placed in the palm of the hand and applied over the entire face.

(B-2) All four fingers of both hands (index finger through pinky) were used to massage two to three times so as to describe a line from the wings of the nose past the mouth (direction opposite A-2).

(B-3) Massaging was done two to three times so as to describe a circle from the outside of the cheeks to the center (direction opposite A-3).

(B-4) Massaging was done two to three times so as to describe an arc from the outside of the forehead to the center (direction opposite A-4).

(B-5) (B-2) through (B-4) were repeated three times.

(B-6) The area under the eyes was massaged toward the inner three times so as to describe a gradual arc (direction opposite A-6).

(B-7) The areas were washed with lukewarm water.

Here, the dermal blood flow was measured with a laser tissue blood flow meter.

For the darkness index, dark to light skin color was divided into ten ranks from 1 to 10 by five experts, and the mean value was used as the darkness index.

For the tightness index, "not tight" to "tight" states were divided into ten ranks from 1 to 10, and the mean value was used as the tightness index.

Figure 4:
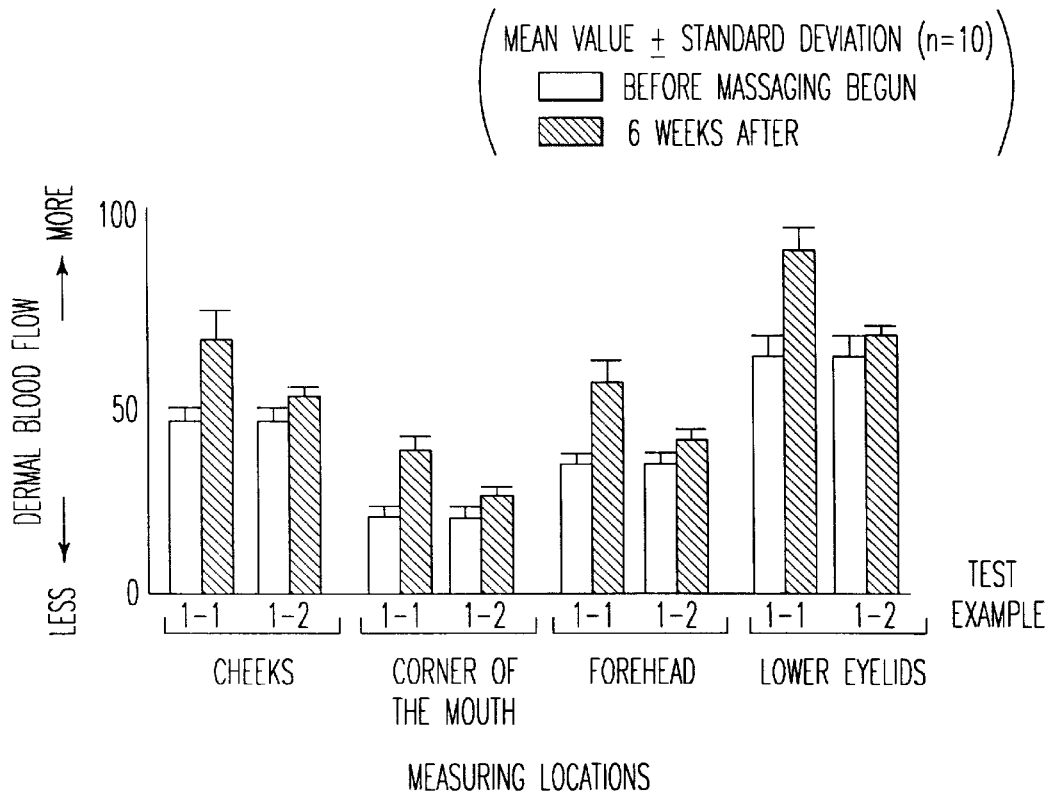
FIG. 4 is a graph depicting the dermal blood flow before massage was begun and 6 weeks after massage was begun.
Figure 5:
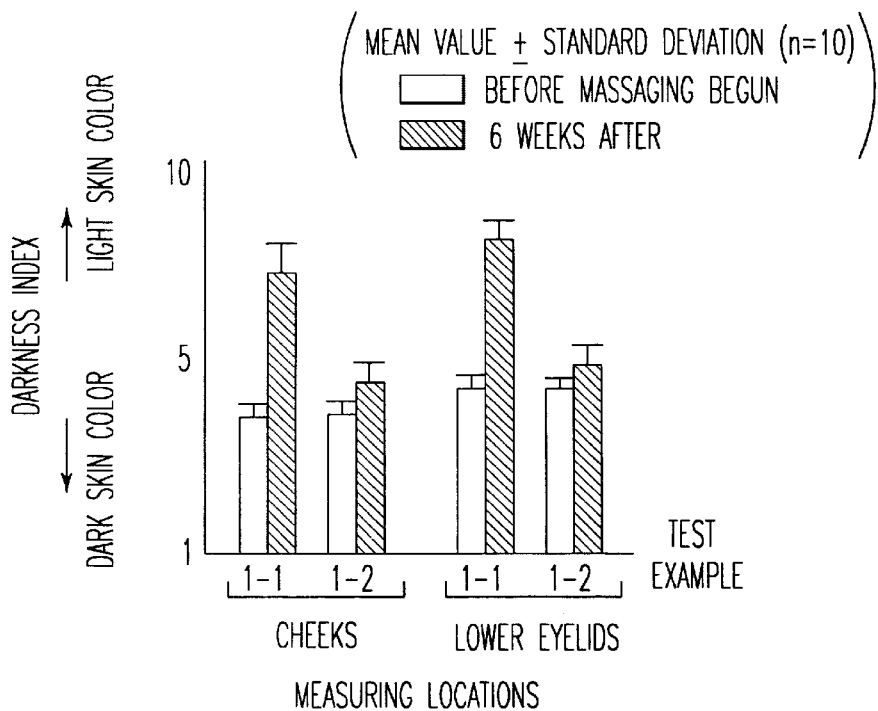
FIG. 5 is a graph depicting the darkness index before massage was begun and 6 weeks after massage was begun.
Figure 6:
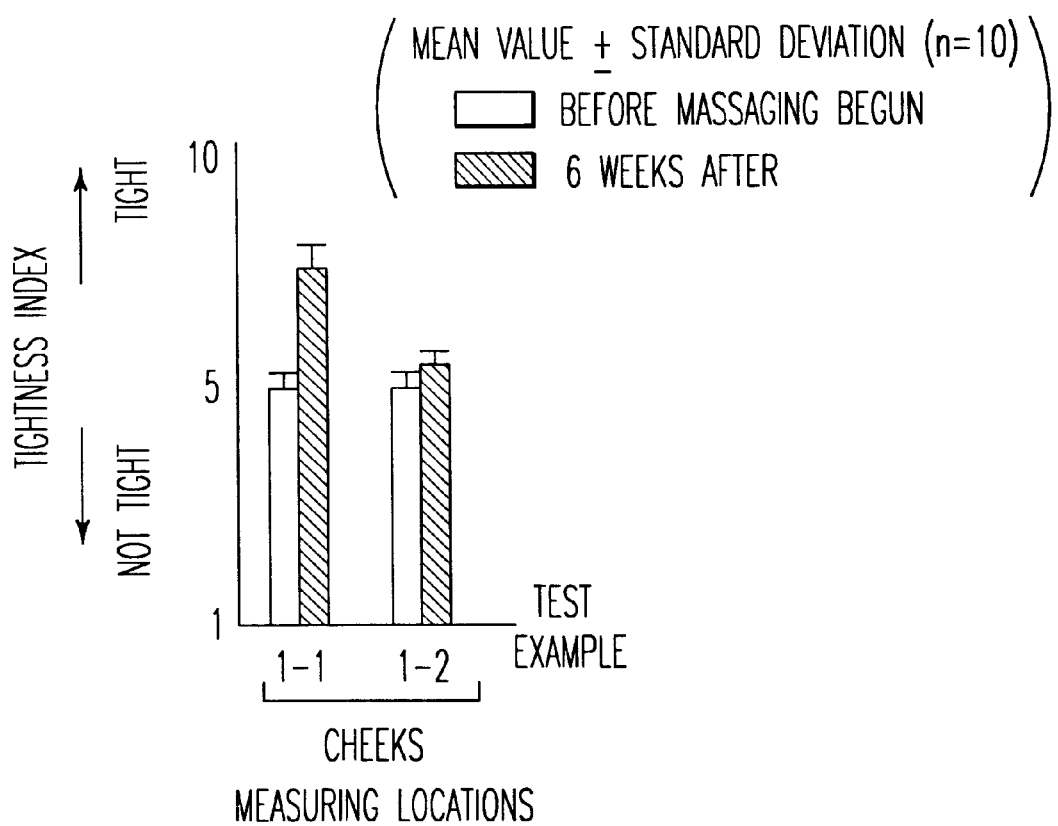
FIG. 6 is a graph depicting the tightness index before massage was begun and 6 weeks after massage was begun.

The results of FIGS. 4 through 6 confirmed that the beauty-treatment method of the present invention, in which massaging was first done in the direction of arterial blood flow and then in the direction of venous blood flow, afforded better cosmetic effects in terms of dermal blood flow, darkness, and tightness than did the beauty-treatment method of the comparative example in which massaging was done in the opposite direction.

Test Example 2

The same method A as that in Test Example 1-1 was carried out using the same composition as in Table 1 as the massaging cosmetic, except that it contained no disintegrating granules or blood circulation promoter, and the dermal blood flow, darkness index, and tightness index were evaluated before and six weeks after massaging was begun (Test Example 2-1).

A cosmetic containing no disintegrating particles or blood circulation promoter was used in the same manner as in Test Example 2-1, except that conventional beauty-treatment methods C (Test Example 2-2) and D (Test Example 2-3) below were carried out, and the dermal blood flow, darkness index, and tightness index were evaluated before and six weeks after massaging was begun. The results are given in FIGS. 7 through 9. These figures combine the results of Test Example 1-1 above for reference.

Method C (Test Example 2-2)

(C-1) Approximately 2 mL cosmetic was placed in the palm of the hand and applied over the entire face.

Figure 19:
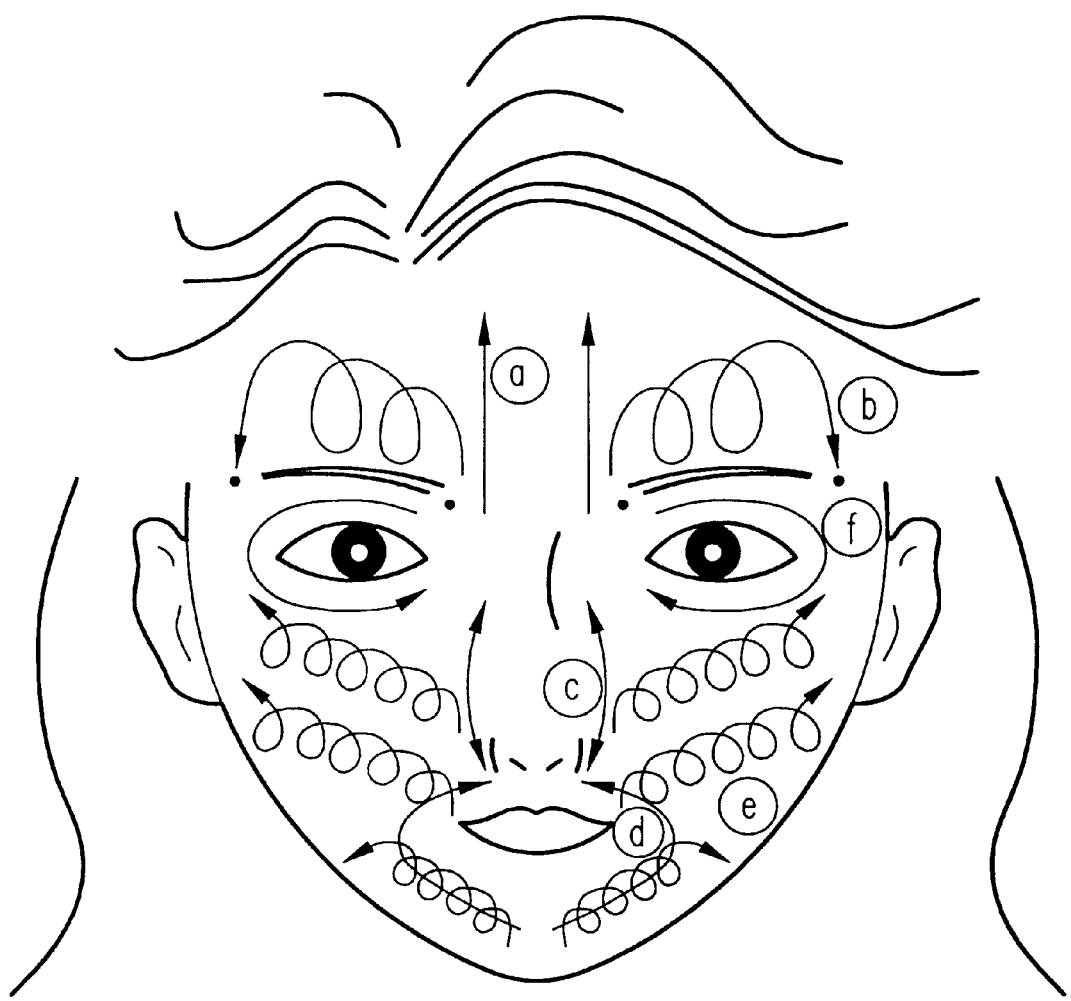
FIG. 19 is an illustration of convention facial massage movements used for Method C in which massaging is done centripetally from a location distant from the heart to a location nearer the heart. This method involves massaging along the vascular distribution, but not along the flow of blood.

(C-2) The forehead was massaged three times from bottom to top by alternately rubbing with both hands, as shown by (a) in FIG. 19.

(C-3) Massaging was done three times so as to describe a spiral from between the eyebrows to the outside as shown by (b).

(C-4) Massaging was done by lightly moving the fingertips three times up from the bottom at the sides of the nose as shown by (c).

(C-5) Massaging was done three times by rubbing around the mouth so as to raise the corners of the mouth as shown by (d).

(C-6) Massaging was done twice by spirally rubbing the cheeks in three stages (top, middle, bottom) as shown by (e).

(C-7) Massaging once around the eyes was done three times as shown by (f).

(C-1) through (C-7) above were done for about 3 to 5 minutes. Method C is a method in which massaging is done centripetally from a location distant from the heart to a location that is near. This method involves massaging along the vascular distribution, but not along the flow of blood.

Method D (Test Example 2-3)

(D-1) Approximately 2 mL cosmetic was placed in the palm of the hand and applied over the entire face.

Figure 20:
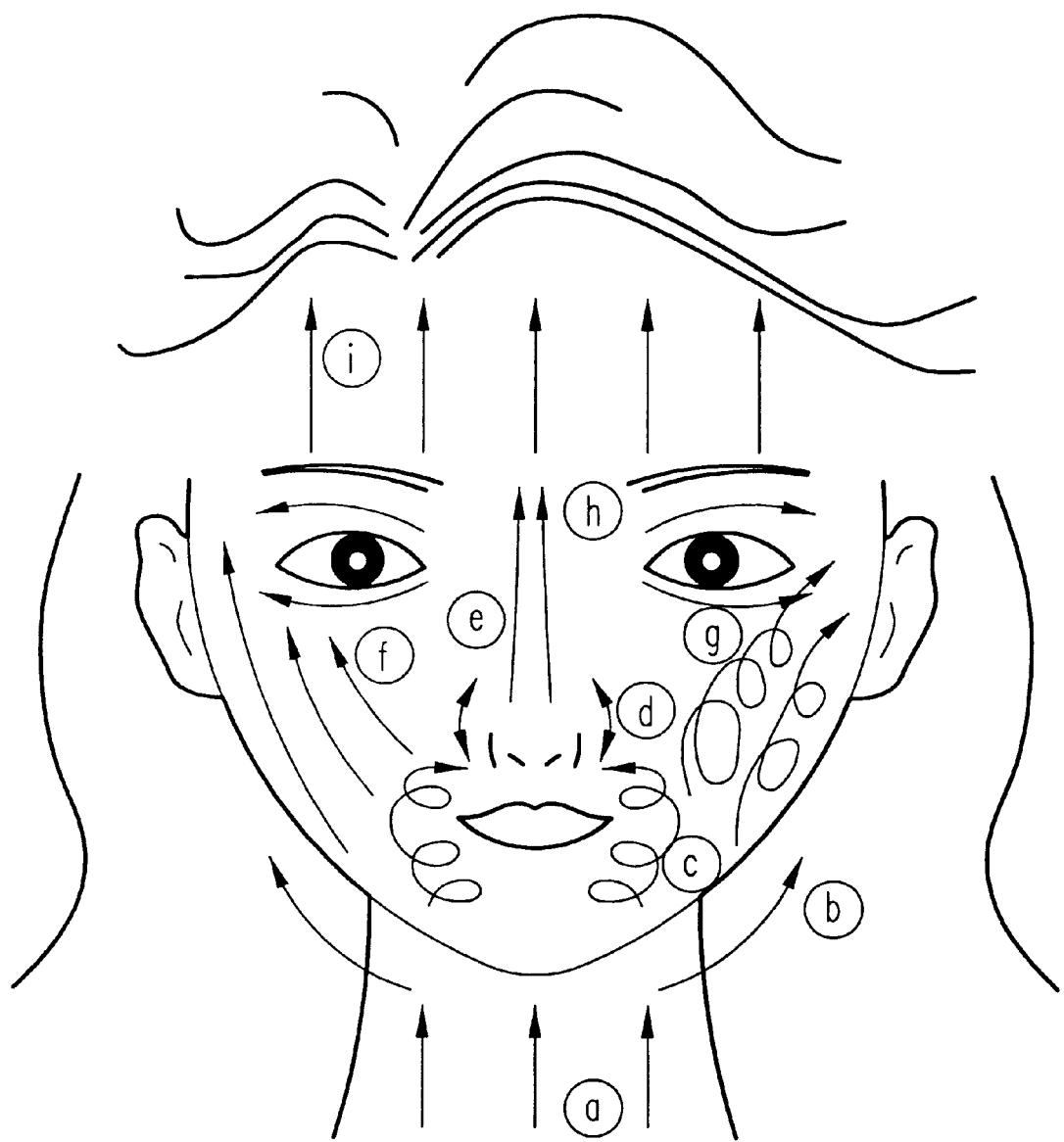
FIG. 20 is an illustration of conventional facial massage movements used in Method D in which massaging is done centrifugally from the heart. This method considers the supply of blood from the heart to the dermal tissue, but does not consider blood flow from the dermal tissue to the heart.

(D-2) Massaging was done three times by alternately rubbing the sides from the center of the neck with the palms of both hands, from the bottom toward the top, as shown by (a) in FIG. 20.

(D-3) Massaging was done three times by placing the index fingers of both hands in the center of the chin and underpart of the lips, and placing the middle finger of both hands in the lower part of the chin, rubbing the index fingers and the middle fingers alternately left and right on the mandible as far as the bottom of the ears as shown by (b).

(D-4) The middle and ring fingers of both hands were placed on the chin, massaging was done so as to describe a spiral toward both ends of the lips, and massaging was further done three times by rubbing toward the top of the lips as shown by (c).

(D-5) Both sides of the wings of the nose were massaged three times from top to bottom with the middle and ring fingers of both hands as shown by (d).

(D-6) Massaging was done three times by rubbing up from the tip of the nose as shown by (e).

(D-7) Massaging was done three times each by rubbing from the sides of the lips and the sides of the wings of the nose or center of the nose toward the temples using the middle and ring fingers as shown by (f).

(D-8) Massaging was done three times each by rubbing from the sides of the lips and the sides of the wings of the nose or center of the nose toward the temples so as to describe a spiral as shown by (g).

(D-9) The cheeks were patted three times in their entirety using all fingers of both hands.

(D-10) The middle and ring fingers were placed on the upper eyelids, and the fingers were gently rubbed while exerting pressure from the inner corners of the eyes toward the outer corners of the eyes as shown by (h).

(D-11) Massaging was done three times by rubbing the entire forehead with the fingertips perpendicularly from the bottom upwards as shown by (i).

(D-1) through (D-11) were done for about 3 to 5 minutes.

Method D is a method in which massaging is done centrifugally from the heart. In this method, the supply of blood from the heart to the dermal tissue is considered, whereas the blood from the dermal tissue to the heart is not considered.

Figure 7:
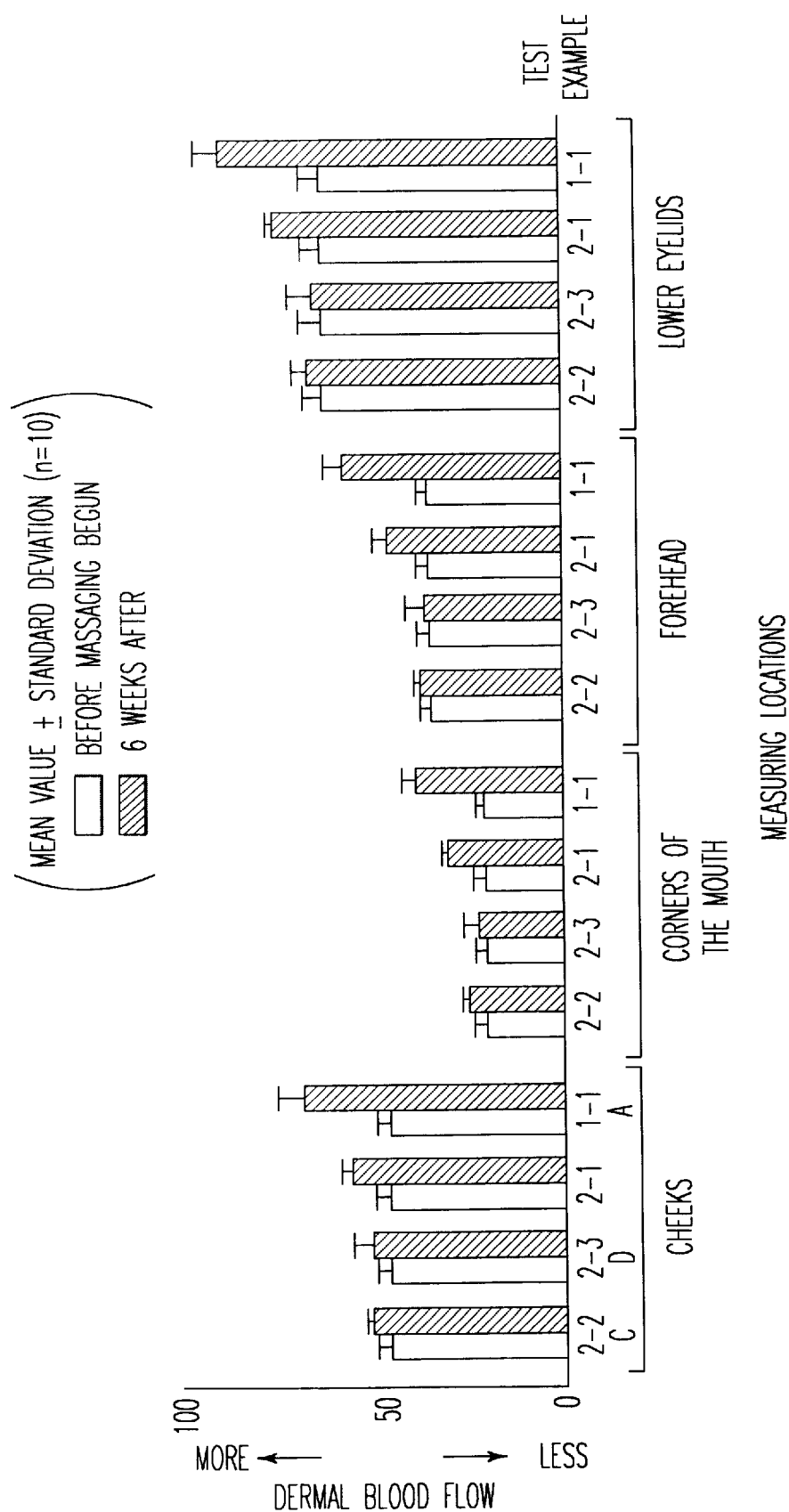
FIG. 7 is a graph depicting the dermal blood flow before massage was begun and 6 weeks after massage was begun.
Figure 8:
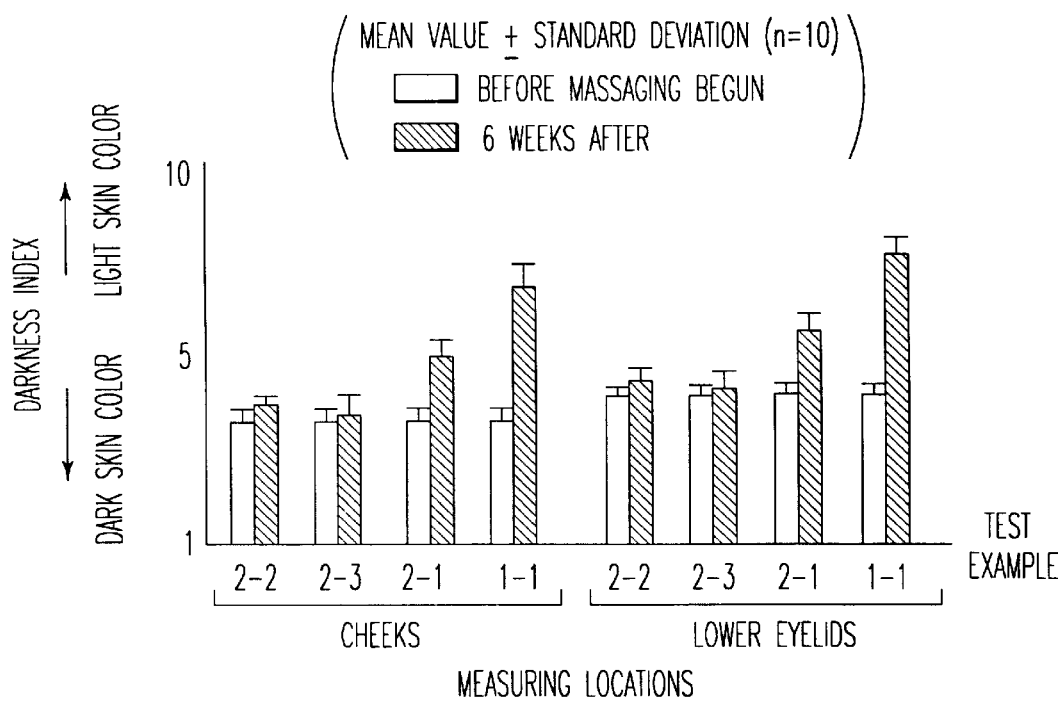
FIG. 8 is a graph depicting the darkness index before massage was begun and 6 weeks after massage was begun.
Figure 9:
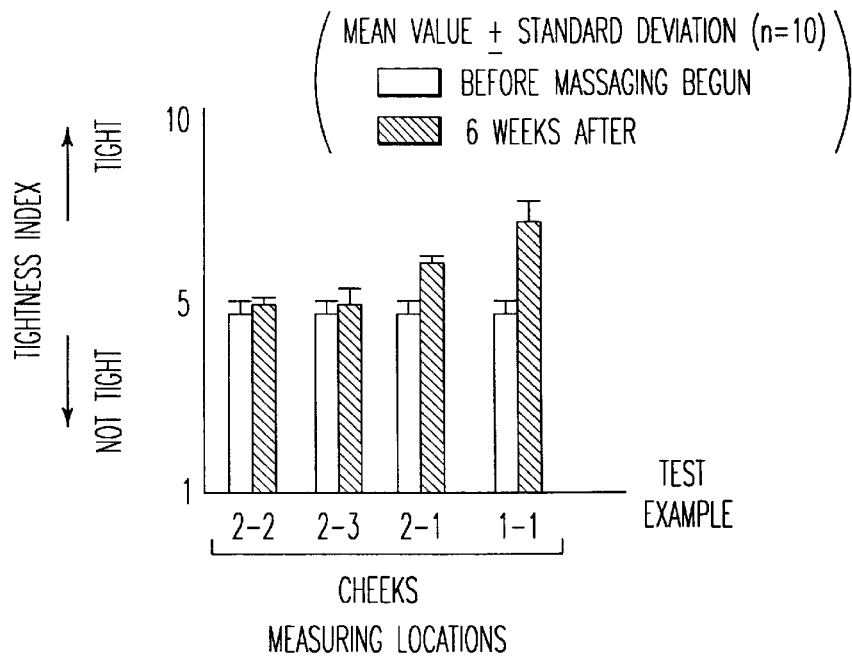
FIG. 9 is a graph depicting the tightness index before massage was begun and 6 weeks after massage was begun.

The results of FIGS. 7 through 9 confirmed that, even without the use of a massaging cosmetic containing disintegrating particles, the beauty-treatment method of the present invention, in which massaging was first done in the direction of arterial blood flow and then in the direction of venous blood flow, afforded better cosmetic effects in terms of dermal blood flow, darkness, and tightness than did the conventional beauty-treatment method in which the direction of the blood circulation was not taken into account.

Test Example 3

Thirty normal females in their forties were divided into three groups A through C, and a beauty-treatment method consisting of the massage in method A of Test Example 1-1 was done once for 30 seconds in each group using a cosmetic having the composition in Table 1 above. This was done once a day for six weeks while the subjects were in a resting state before washing their faces upon rising in the morning in Group A (Test Example 3-1), while the subjects were bathing in Group B (Test Example 3-2), and after the subjects had jogged 3 km for 20 minutes in Group C (Test Example 3-3).

Here, the pulse and skin temperature were measured when the massage was begun, that is, during the actual massage, in each group. The results are given in Table 2.

The dermal blood flow, darkness index, and tightness index were determined and compared as shown below before and six weeks after massaging was begun in the same way as Test Example 1. The results are given in FIGS. 10 through 12.

TABLE 2

|  | State during massage | Pulse (beat/min) | Skin temp. (° C.) |
|---|---|---|---|
| Group A (Test Ex. 3-1) | resting state upon rising | 70.2 ± 5.31 | 33.5 ± 0.04 |
| Group B (Test Ex. 3-2) | during bath | 120 ± 9.62 | 36.3 ± 0.07 |
| Group C (Test Ex. 3-3) | after jogging | 140 ± 10.5 | 37.4 ± 0.09 |

Figure 10:
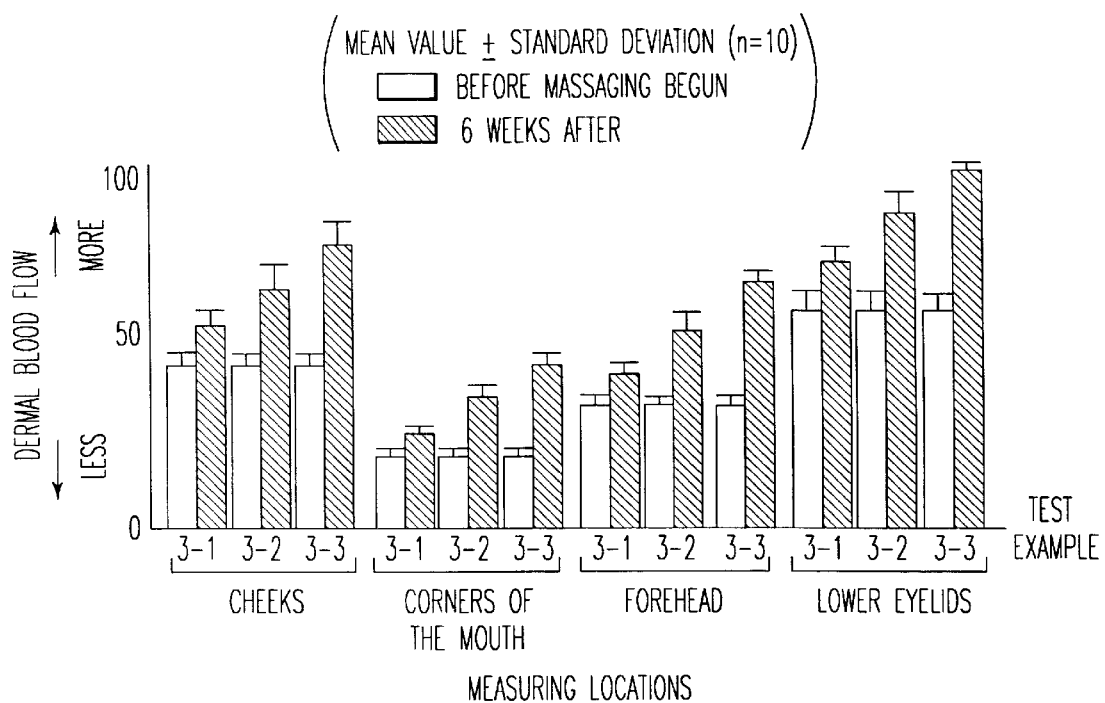
FIG. 10 is a graph depicting the dermal blood flow before massage was begun and 6 weeks after massage was begun.
Figure 11:
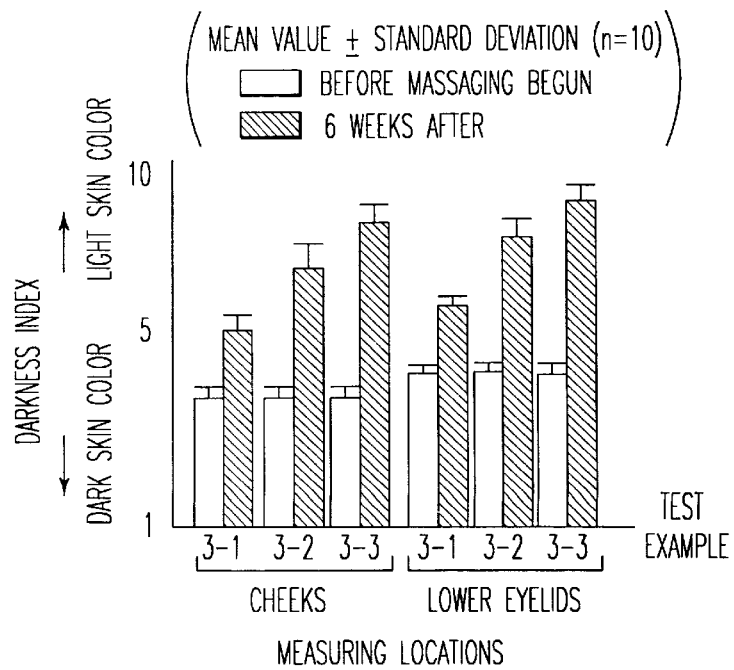
FIG. 11 is a graph depicting the darkness index before massage was begun and 6 weeks after massage was begun.
Figure 12:
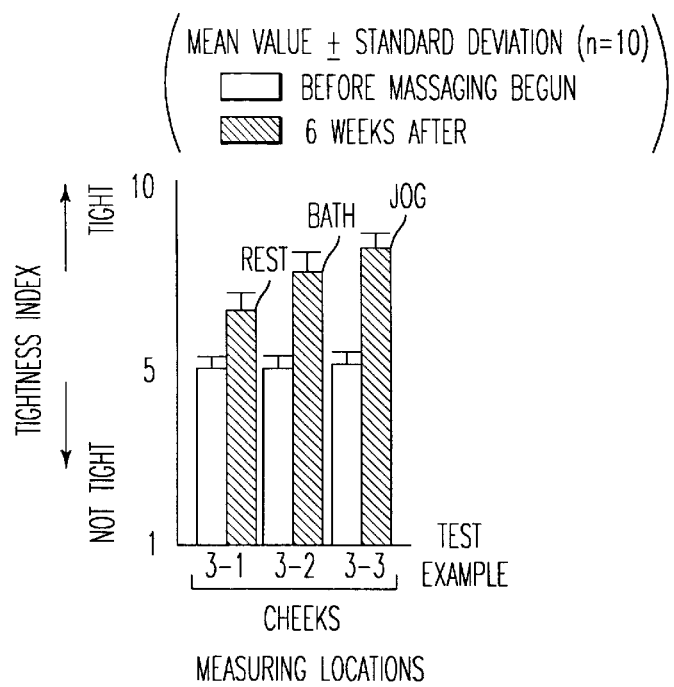
FIG. 12 is a graph depicting the tightness index before massage was begun and 6 weeks after massage was begun.

Table 2 shows that stimulated pulse and skin temperature were in the following order: Group C>Group B>Group A. The results in FIGS. 10 through 12 show the effects of stimulated dermal blood flow as a result of massage, the effects of less darkness, and the effects of improvement in tightness in the following order: Group C>Group B>Group A. It could thus be confirmed that better cosmetic effects from massaging were obtained when the pulse or the like was stimulated.

Test Example 4

The same massaging as that described above was done in Groups A (Test Example 4-1), B (Test Example 4-2), and C (Test Example 4-3) using a cosmetic having the same composition as that in Table 1 as the massaging cosmetic except that it contained no disintegrating particles or blood circulation promoters, and the dermal blood flow, darkness index, and tightness index were evaluated before and six weeks after massaging was begun. The results are given in FIGS. 13 through 15.

Figure 13:
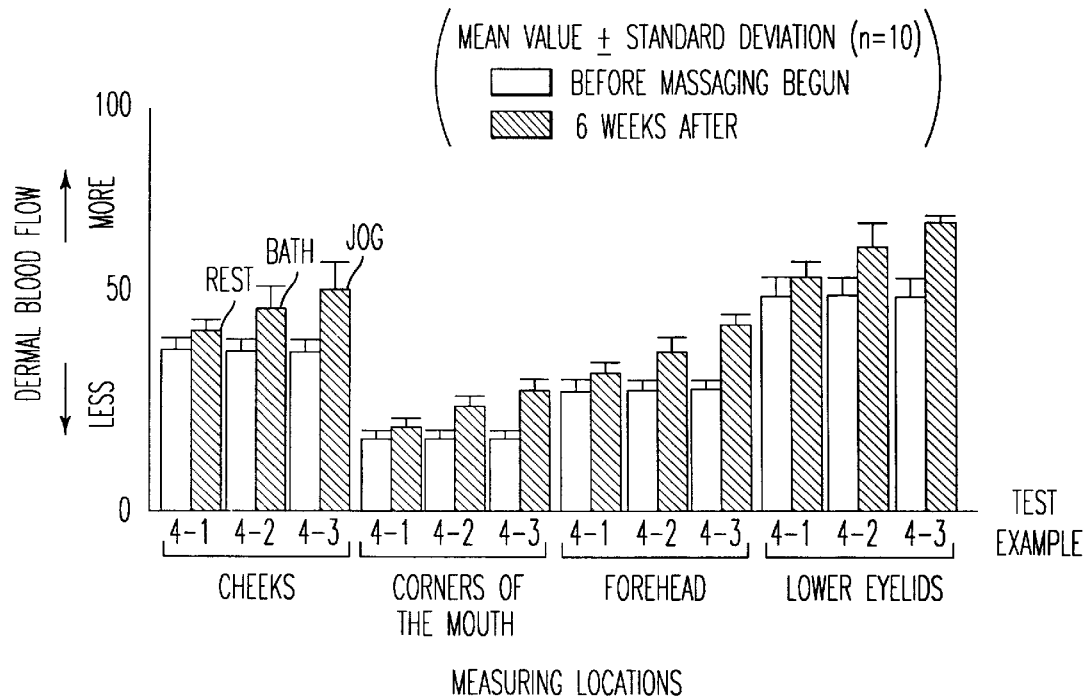
FIG. 13 is a graph depicting the dermal blood flow before massage was begun and 6 weeks after massage was begun.
Figure 14:
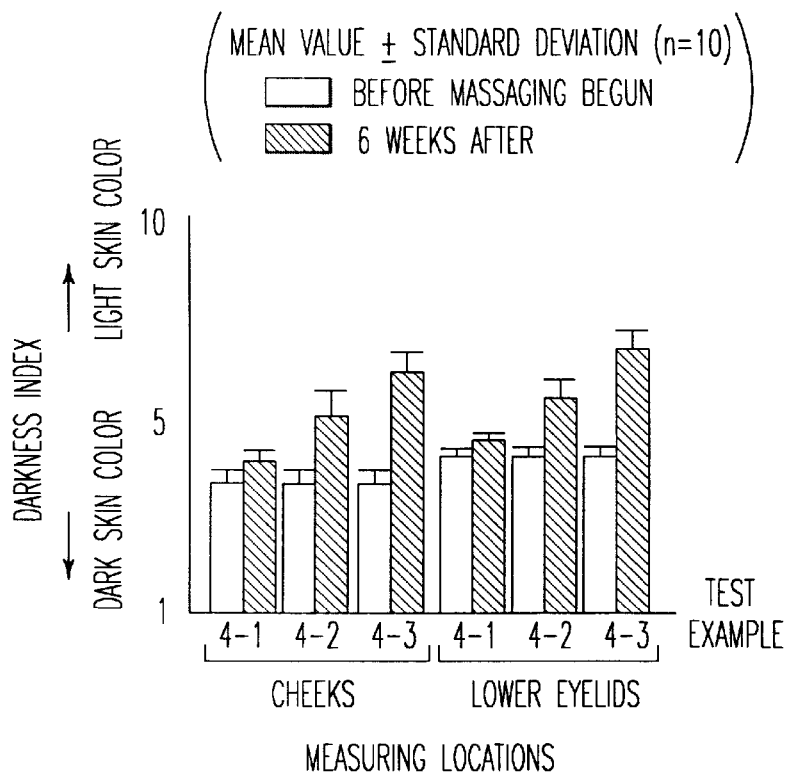
FIG. 14 is a graph depicting the darkness index before massage was begun and 6 weeks after massage was begun.
Figure 15:
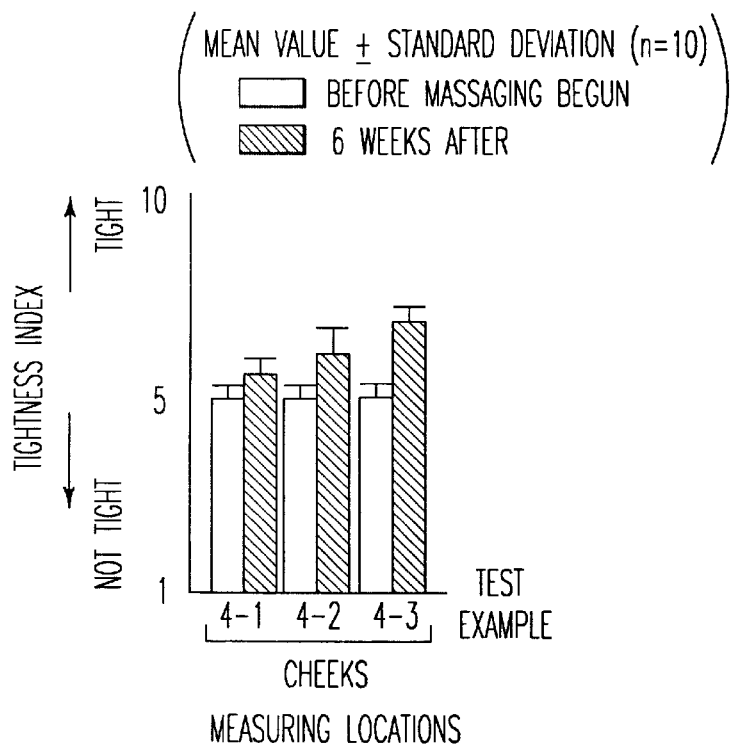
FIG. 15 is a graph depicting the tightness index before massage was begun and 6 weeks after massage was begun.

FIGS. 13 through 15 show that, when the massaging cosmetic including no disintegrating particles or blood circulation promoters were used, the effects of stimulated dermal blood flow, the effects of less darkness, and the effects of improvement in tightness were in the following order: Group C>Group B>Group A, which was the same order as the stimulated pulse and the like during massage, and that better cosmetic effects from massaging were obtained in groups C and B, which had stimulated pulse levels and the like during massage, than when at rest in group A. However, the cosmetic effects resulting from the massage did not improve as much as in the aforementioned Test Examples 3-3 and 3-2, where cosmetics containing disintegrating particles and blood circulation promoters were used. It may thus be seen that the use of cosmetics containing disintegrating particles and blood circulation promoters as a massaging cosmetic is preferred.

Test Example 5

Twenty normal females in their thirties were divided into two groups A and B, a cosmetic method consisting of the following cosmetic step A (Test Example 5-1) or B (Test example 5-2) was used on skin where foundation had been applied, and the (i) corneal layer moisture content, (ii) amount of sebum restoration, and (iii) feeling of stiffening were evaluated as follows. The results are given in FIGS. 16 through 18.

Cosmetic Step A (Test Example 5-1)

(A-1) Cleansing: 2 g cosmetic having the composition shown in Table 3 was used as a cleansing cosmetic, this was applied over the entire face, and it was washed off with water.

TABLE 3

| Cleansing cosmetic | (wt %) |
|---|---|
| polyoxyethylene octyl dodecyl ether (20 E.O.) (ELB = 13) | 12.5 |
| stearyl trimethylammonium chloride | 0.3 |
| polyoxyethylene methyl glyceride (10 E.O.) | 15.0 |
| 2-ethylhexanoic acid triglyceride | 12.5 |
| polyisobutene (pentamer) | 12.5 |
| sorbitol | 33.3 |
| methylparaben | 0.1 |
| butylparaben | 0.1 |
| perfume | 0.1 |
| purified water | 13.9 |

(A-2) Massage: The massage in method A of Test Example 1-1 was done for 30 seconds using the aforementioned massaging cosmetic having the composition in Table 1 as the massaging cosmetic.

(A-3) Washing face with detergent: 1 mL of the facial detergent having the composition given in Table 4 was placed in the palm of the hand, this was applied to the entire face and lathered, and it was washed off with water.

TABLE 4

| Facial detergent | (wt %) |
|---|---|
| alkyl saccharide (*2) | 10.0 |
| triethanolamine myristate | 10.0 |
| lauryl dimethylamine oxide | 3.0 |
| propylene glycol | 5.0 |
| glycerol | 5.0 |
| denatured ethanol | 3.0 |
| ethylene glycol distearyl | 3.0 |
| polyoxyethylene (9)-sec-tetradecyl ether | 1.0 |
| deionized water | 60.0 |

(*2) Alkyl saccharide: structural formula $R^1$—O—$(G)_n$ where $R^1$ = $C_{10}H_{21}$, G = glucose, and n = 1.5

(A-4) Use of skin lotion: 1 mL of a cosmetic having the composition given in Table 5 was placed in the palm of the hand as skin lotion, and it was applied to the entire face.

TABLE 5

| Skin lotion | (wt %) |
|---|---|
| glycerol | 5.0 |
| propylene glycol | 4.0 |
| oleyl alcohol | 0.1 |
| polyoxyethylene sorbitan monolauric acid ester (20 E.O.) | 1.5 |
| polyoxylauryl ether (20 E.O.) | 0.5 |
| ethanol | 10.0 |
| perfume | 0.1 |
| dye | as needed |
| preservative | as needed |
| purified water | 78.8 |

(A-5) Use of emulsion: 1 mL of a cosmetic as emulsion having the composition given in Table 6 was placed in the palm of the hand and applied to the entire face.

TABLE 6

| Emulsion | (wt %) |
| --- | --- |
| stearic acid | 0.2 |
| cetanol | 1.5 |
| vaseline | 3.0 |
| lanolin alcohol | 2.0 |
| liquid paraffin | 10.0 |
| polyoxyethylene monooleic acid ester (10 E.O.) | 2.0 |
| perfume | 0.5 |
| preservative, antioxidant | as needed |
| glycerol | 3.0 |
| propylene glycol | 5.0 |
| triethanolamine | 1.0 |
| purified water | 70.0 |

Cosmetic Step B (Test Example 5-2)

(A-2) The steps were carried out in sequence in the same manner as in cosmetic step A except that no massaging was done.

Evaluation Parameters (i) Corneal Layer Moisture Content

The dermal conductance was determined with a conductance meter as an index of the corneal layer moisture content.

(ii) Amount of Sebum Restoration

The amount of squalane on the surface of the skin was measured by gas chromatography as an index of the amount of sebum restoration.

(iii) Feeling of stiffening

The subjects evaluated "stiffening" to "not stiffening" in five ranks, the mean for each group was determined, and this was used as the tightness index.

Figure 16:
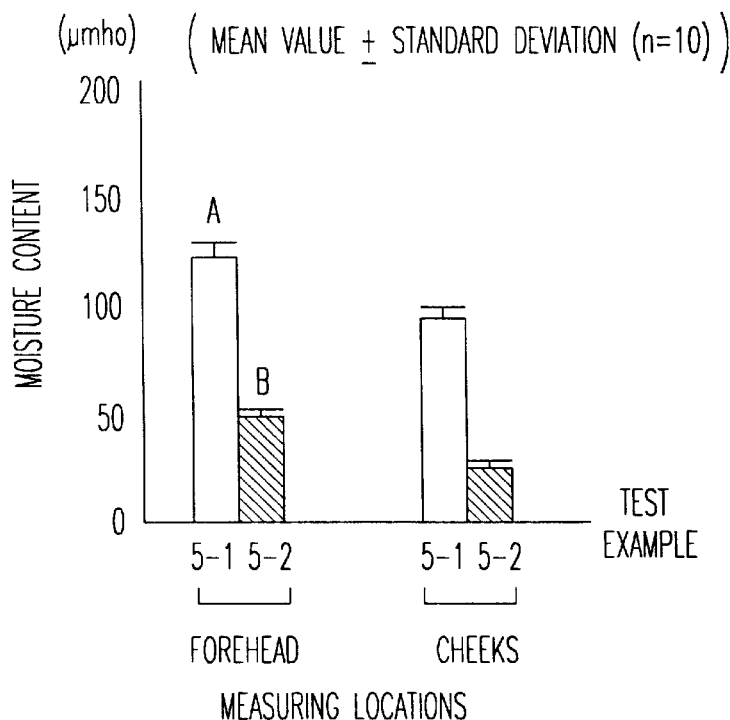
FIG. 16 is a graph depicting the moisture content of the corneal layer after implementing the cosmetic method.
Figure 17:
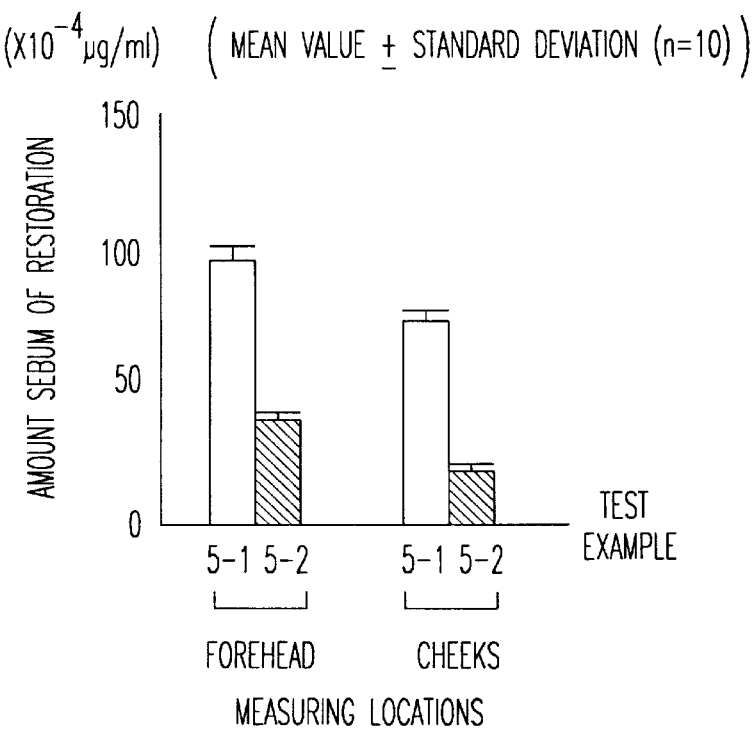
FIG. 17 is a graph depicting the amount of sebum restoration after implementing the cosmetic method.
Figure 18:
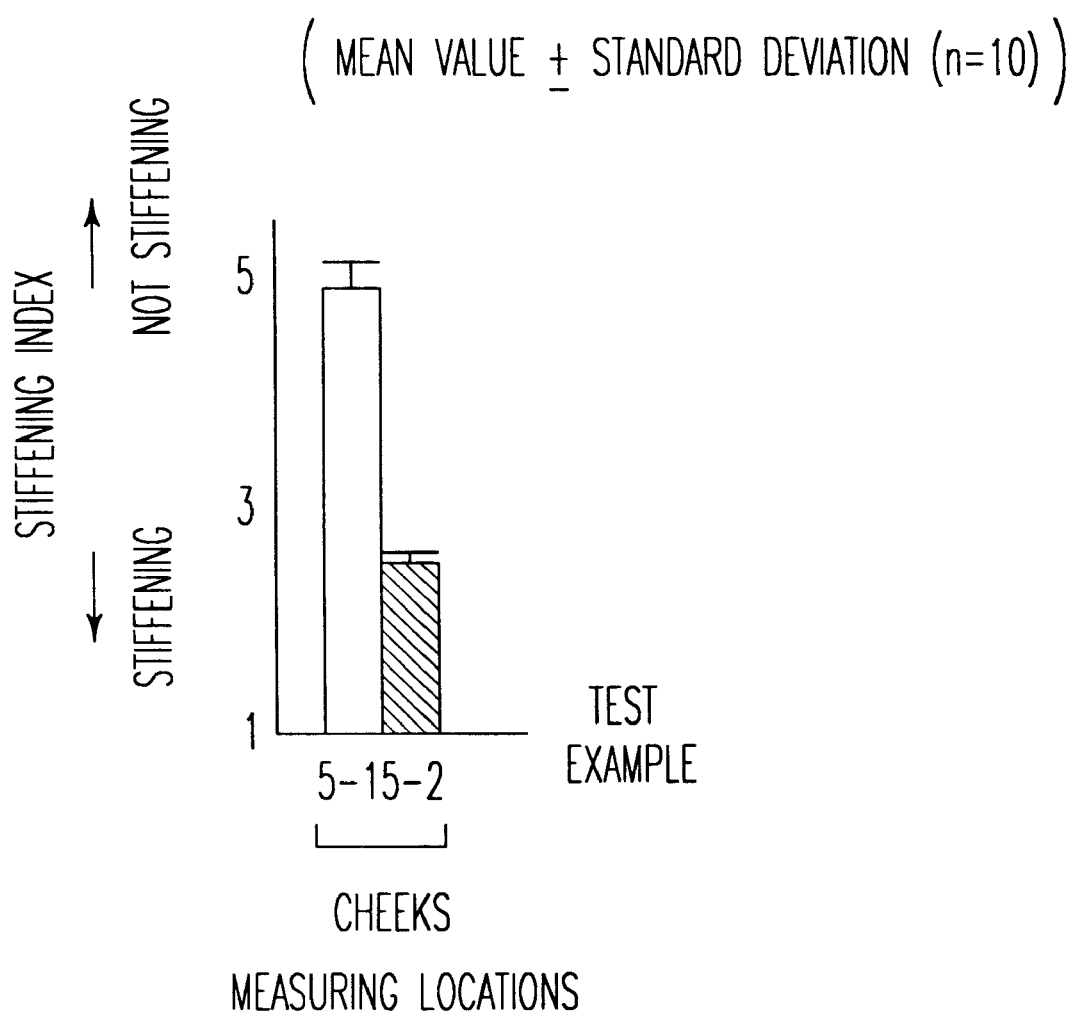
FIG. 18 is a graph depicting the stiffening index after implementing the cosmetic method.

FIGS. 16 through 18 show that sebum was restored more rapidly, the corneal layer moisture retention was better, there was no feeling of stiffening, and there was far greater skincare cosmetic action when massaging was done with the use of a massaging cosmetic containing disintegrating particles before the use of skin lotion and emulsion skincare cosmetics than when a skincare cosmetic was used without such massaging.

INDUSTRIAL APPLICABILITY

In the first or second beauty-treatment method pertaining to the present invention, massaging can be readily done even by ordinary people, and considerable cosmetic effects can be obtained as a result of the massage. More specifically, a variety of effects can be obtained, including the promotion of blood circulation, better skin color, less swelling, the prevention or eradication of pimples, the prevention of cosmetic defects, better skin tightness, improvement of slackness, and better cosmetic application. As such, the beauty-treatment method pertaining to the present invention is useful as a method of daily skincare.

In the cosmetic method pertaining to the present invention, a skincare cosmetic is used after washing, allowing more effective use of the skincare cosmetic to be achieved. It is thus possible to enhance the moisture retention function of the corneal layer of the skin, promote regeneration of the moist components of the skin, improve skin softness, improve tightness or slackness, improve cosmetic application, and prevent cosmetic defects.

What is claimed is:

1. A beauty-treatment method, comprising, or comprising the steps of:

massaging a massaging location first in the direction of arterial blood flow on a human body or face;

and then massaging in the direction of venous blood flow.

2. A beauty-treatment method as defined in claim 1, wherein the massaging location is massaged with the use of cosmetic.

3. A beauty-treatment method as defined in claim 2, wherein the cosmetic comprises disintegrating particles.

4. A beauty-treatment method as defined in claim 3, wherein the cosmetic comprises a blood circulation promoter.

5. A beauty-treatment method as defined in claim 3, wherein the cosmetic comprises an oil with a refractive index of at least 1.444 or an SP value of at least 16.5.

6. A beauty-treatment method as defined in claim 3, wherein the cosmetic comprises a cosmetic whitener.

7. A beauty-treatment method as defined in claim 3, wherein the cosmetic comprises a sebum secretion inhibitor.

8. A cosmetic method for washing skin with a detergent and then applying a skin care cosmetic, which comprises administering a massage with a massaging cosmetic comprising disintegrating particles before the skin care cosmetic is used and after the skin is washed with the detergent, and wherein the administering of the massage comprises massaging a massaging location first in the direction of arterial blood flow, and then massaging in the direction of venous blood flow.

9. A cosmetic method for washing skin with a cleanser and a detergent, and then applying a skin care cosmetic, wherein said cosmetic method comprises administering a massage with a massaging cosmetic comprising disintegrating particles before the skin care cosmetic is used and after the skin is washed with the cleanser or detergent, and wherein the administering of the massage comprises massaging a massaging location first in the direction of arterial blood flow, and then massaging in the direction of venous blood flow.

* * * * *